US009387055B2

(12) United States Patent
Cinader, Jr. et al.

(10) Patent No.: US 9,387,055 B2
(45) Date of Patent: Jul. 12, 2016

(54) METHODS AND APPARATUS FOR APPLYING DENTAL SEALANT TO AN ORTHODONTIC PATIENT'S TEETH

(75) Inventors: David K. Cinader, Jr., Walnut, CA (US); James K. Mah, Los Angeles, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 1091 days.

(21) Appl. No.: 12/743,634

(22) PCT Filed: Nov. 20, 2008

(86) PCT No.: PCT/US2008/084127
§ 371 (c)(1),
(2), (4) Date: May 19, 2010

(87) PCT Pub. No.: WO2009/070480
PCT Pub. Date: Jun. 4, 2009

(65) Prior Publication Data
US 2010/0279243 A1  Nov. 4, 2010

Related U.S. Application Data

(60) Provisional application No. 60/991,041, filed on Nov. 29, 2007.

(51) Int. Cl.
*A61C 3/00* (2006.01)
*A61C 7/14* (2006.01)
*A61C 7/16* (2006.01)

(52) U.S. Cl.
CPC .. *A61C 7/146* (2013.01); *A61C 7/16* (2013.01)

(58) Field of Classification Search
CPC ............ A61C 7/146; A61C 7/08; A61C 7/00; A61C 7/12; A61C 7/14; A61C 7/16; A61C 19/003; A61C 8/0013
USPC ........................................................ 433/2–24
See application file for complete search history.

(56) References Cited

U.S. PATENT DOCUMENTS

| 3,738,005 | A | * | 6/1973 | Cohen et al. ...................... 433/3 |
| 3,814,717 | A | | 6/1974 | Wilson et al. |
| 3,949,477 | A | | 4/1976 | Cohen et al. |
| 3,994,761 | A | * | 11/1976 | Higbee ........................ 156/145 |

(Continued)

FOREIGN PATENT DOCUMENTS

WO    WO 00/69393    11/2000

OTHER PUBLICATIONS

U.S. Appl. No. 60/869,741, filed Dec. 13, 2006 entitled "Methods of Using a Dental Composition Having an Acidic Component and a Photobleachable Dye".

(Continued)

*Primary Examiner* — Cris L Rodriguez
*Assistant Examiner* — Mirayda A Aponte

(57) ABSTRACT

A set of orthodontic appliances is releasably connected to wall portions of a bonding tray that is used in an indirect bonding procedure. A quantity of dental sealant is applied to wall portions of the tray, and is subsequently transferred to enamel surfaces of the patient s teeth when the bonding tray is placed in position over one of the patient s dental arches. The dental sealant tends to reduce the formation of plaque in regions of the patient s tooth surfaces adjacent the orthodontic appliances.

20 Claims, 13 Drawing Sheets

(56) References Cited

U.S. PATENT DOCUMENTS

| | | | |
|---|---|---|---|
| 4,812,118 A | 3/1989 | Creekmore | |
| 5,015,180 A | 5/1991 | Randklev | |
| 5,114,339 A | 5/1992 | Guis | |
| 5,172,809 A | 12/1992 | Jacobs et al. | |
| 5,354,199 A | 10/1994 | Jacobs et al. | |
| 5,429,229 A | 7/1995 | Chester et al. | |
| 5,538,129 A | 7/1996 | Chester et al. | |
| 5,971,754 A | 10/1999 | Sondhi et al. | |
| 6,050,815 A | 4/2000 | Adam et al. | |
| 6,126,922 A | 10/2000 | Rozzi et al. | |
| 6,183,249 B1 | 2/2001 | Brennan et al. | |
| 6,331,080 B1 | 12/2001 | Cole et al. | |
| 6,444,725 B1 | 9/2002 | Trom et al. | |
| 6,474,990 B1* | 11/2002 | Hoffman | 433/91 |
| 6,528,555 B1 | 3/2003 | Nikutowski et al. | |
| 6,960,079 B2 | 11/2005 | Brennan et al. | |
| 7,020,963 B2* | 4/2006 | Cleary et al. | 29/896.11 |
| 7,188,421 B2 | 3/2007 | Cleary et al. | |
| 7,364,428 B2 | 4/2008 | Cinader, Jr. et al. | |
| 7,845,938 B2* | 12/2010 | Kim et al. | 433/3 |
| 7,910,632 B2* | 3/2011 | Cinader et al. | 523/118 |
| 8,246,351 B2* | 8/2012 | Huang | 433/24 |
| 8,308,478 B2* | 11/2012 | Primus et al. | 433/24 |
| 2003/0196914 A1 | 10/2003 | Tzou et al. | |
| 2005/0136370 A1 | 6/2005 | Brennan et al. | |
| 2005/0175965 A1 | 8/2005 | Craig et al. | |
| 2005/0175966 A1 | 8/2005 | Falsafi et al. | |
| 2005/0176844 A1 | 8/2005 | Aasen et al. | |
| 2006/0084026 A1 | 4/2006 | Cinader et al. | |
| 2006/0093990 A1* | 5/2006 | Stone et al. | 433/92 |
| 2006/0134580 A1 | 6/2006 | Raby et al. | |
| 2006/0199147 A1* | 9/2006 | Mahlmann | 433/96 |
| 2006/0257821 A1 | 11/2006 | Cleary et al. | |
| 2007/0015104 A1 | 1/2007 | Wiechmann et al. | |
| 2007/0031774 A1 | 2/2007 | Cinader, Jr. et al. | |
| 2007/0287120 A1 | 12/2007 | Cinader et al. | |
| 2007/0298364 A1 | 12/2007 | Cinader, Jr. | |
| 2008/0096150 A1 | 4/2008 | Cinader, Jr. | |

OTHER PUBLICATIONS

ASTM D 412.
Search Report for PCT/US2008/084127.
Written Opinion for PCT/US2008/084127.

* cited by examiner

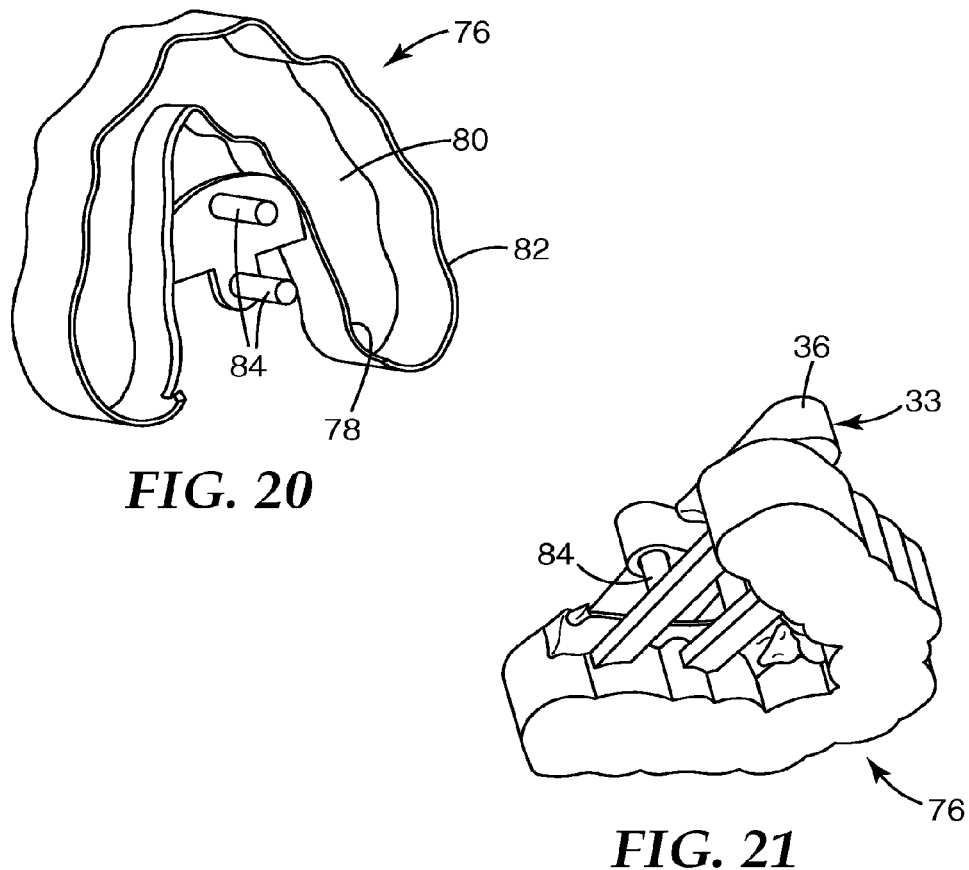
FIG. 20
FIG. 21
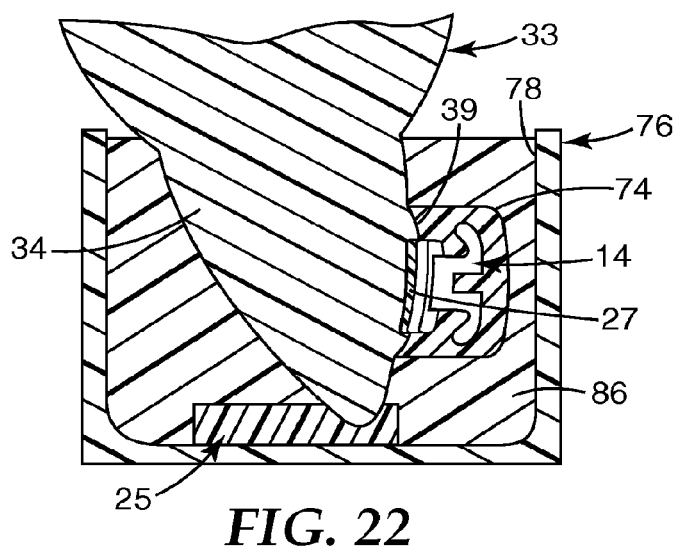
FIG. 22

METHODS AND APPARATUS FOR APPLYING DENTAL SEALANT TO AN ORTHODONTIC PATIENT'S TEETH

CROSS REFERENCE TO RELATED APPLICATIONS

This application is a national stage filing under 35 U.S.C. 371 of PCT/US2008/084127, filed Nov. 20, 2008, which claims priority to U.S. Application No. 60/991,041, filed Nov. 29, 2007, the disclosure of which is incorporated by reference in its/their entirety herein.

BACKGROUND OF THE INVENTION

1. Field of the Invention

This invention broadly relates to methods and apparatus for applying a dental sealant to the enamel tooth surfaces of a patient that is undergoing orthodontic treatment.

2. Description of the Related Art

Orthodontic treatment is often recommended for dental patients that have crowded or crooked teeth, or have teeth that are not properly aligned with other teeth in the oral cavity. Orthodontic treatment can greatly improve a patient's facial appearance, especially in regions near the front of the patient's oral cavity. Orthodontic treatment can also improve the patient's bite so that the teeth function better with each other during chewing and speaking.

One type of orthodontic treatment involves the use of tiny fixed appliances known as brackets that are secured to the patient's anterior teeth by an orthodontic adhesive. A resilient archwire is placed in a slot of each bracket and forms a track to guide movement of the teeth to desired locations. Ends of the archwire are often connected to small appliances known as buccal tubes that are secured to the patient's molar teeth. In some instances, buccal tubes are not directly bonded to the surfaces of the patient's molar teeth but are instead welded or brazed to small metallic bands that, in turn, are placed over the molar teeth in encircling relation.

Often, a set of brackets, buccal tubes and an archwire is provided for each of the patient's upper and lower dental arches. The brackets, buccal tubes and archwires are commonly referred to collectively as "braces". In many instances, braces are worn by patients for a period of time extending from one to two years.

Unfortunately, the presence of braces increases the difficulty of maintaining good oral hygiene during the course of orthodontic treatment. The brackets, buccal tubes and archwires significantly hinder access to adjacent regions of the tooth enamel and may prevent the bristles of a toothbrush from efficiently removing plaque from the tooth surfaces. In addition, the brackets, buccal tubes and archwires often present numerous small recesses and cavities that can trap particles of food.

Acids produced by oral bacteria found in dental plaque can dissolve away portions of the mineral content of teeth. In addition to adversely affecting the quality of the tooth mineral, the demineralization process can change the appearance of the tooth enamel. Areas where demineralization occurs often cause the tooth enamel to take on an opaque white-ish color, which represents an early stage of tooth decay formation known as "white spot lesions".

However, regions of the patient's tooth enamel that are covered by orthodontic brackets during treatment are usually protected from plaque accumulation and will not significantly change in appearance. As a consequence, when the brackets are removed from the teeth at the conclusion of orthodontic treatment, those portions of the tooth enamel that were previously located under the brackets will have a different appearance than the adjacent areas where white spot lesions have been formed. Oftentimes, the white spot lesions will outline the original positions of the orthodontic brackets and spoil the cosmetic appearance of the teeth.

Many suggestions have been made in the past for reducing the accumulation of dental plaque during orthodontic treatment. Special brushes have been developed with relatively narrow, bristled cleaning tips for accessing the small spaces adjacent orthodontic appliances. The use of dental floss is also recommended, although the archwires can hinder access to interproximal spaces. Unfortunately, many orthodontic patients including adolescent patients do not spend sufficient time in maintaining good oral hygiene practices to avoid the formation of plaque while the orthodontic appliances are in place.

As a result, some dentists apply a coating of a dental sealant to the tooth enamel of orthodontic patients to help protect the tooth surfaces from decay. Dental sealants provide a hard coating over the enamel surfaces and can serve as a barrier that protects the enamel from decay-causing bacteria. In some instances, the dentist may use a small applicator such as a brush to coat the exposed areas of the teeth after the brackets and buccal tubes have been secured in place. In other instances, the enamel tooth surfaces are coated with a sealant before the brackets and buccal tubes are installed in place.

SUMMARY OF THE INVENTION

The present invention is directed toward new methods and apparatus for applying a dental sealant to the tooth surfaces of a patient that is involved in orthodontic treatment. To this end, an indirect bonding tray is provided for placing orthodontic appliances on the patient's teeth at the beginning of treatment, and the indirect bonding tray carries a quantity of a dental sealant that is transferred to the patient's teeth at the same time that the orthodontic appliances are placed on the patient's teeth.

In more detail, the present invention in one aspect is directed to orthodontic treatment apparatus that comprises an indirect bonding tray including wall portions having a configuration that matches the configuration of at least some regions of a patient's dental arch. The treatment apparatus also includes a set of orthodontic appliances that are releasably connected to the wall portions. A dental sealant extends across at least some of the wall portions in areas next to the appliances for transfer to the patient's tooth structure when the indirect bonding tray is placed over the patient's dental arch.

Another aspect of the present invention is directed toward a method of providing articles for orthodontic treatment. The method comprises:

making an indirect bonding tray with wall portions having a configuration that matches the configuration of at least some regions of a patient's dental arch, wherein the act of making the indirect bonding tray includes the act of providing a releasable connection between a set of orthodontic appliances and the wall portions; and applying a dental sealant to at least some of the wall portions in areas next to the appliances.

The present invention is an advantage in that dental sealant can be applied to the patient's teeth at the same time that orthodontic appliances are secured to the patient's teeth. This results in a considerable savings of time for both the practitioner and the patient because the dental sealant need not be applied during an earlier or later manual procedure using, for example, a small brush. In a preferred embodiment of the invention, essentially all of the inner wall portions of the bonding tray are coated with a layer of dental sealant to help ensure that essentially all exposed areas of the patient's teeth receive a quantity of the sealant.

Advantageously, the dental sealant may also serve as a lubricant for facilitating movement of the tray into its proper position on the patient's dental arch during a bonding procedure. This advantage is especially important when the inner wall portions of the bonding tray are made of a matrix material that otherwise would not easily slide across the surfaces of the teeth. Lubricant properties of the dental sealant increase the likelihood that each of the orthodontic appliances is bonded to the patient's teeth at its precise intended location, and may also help ensure that the bonding adhesive that is coated onto the base of the appliances is not unduly shifted or otherwise disturbed.

An additional advantage of the present invention is that the indirect bonding tray may help reduce the effects of oxygen inhibition of the dental sealant when certain sealants are used. Wall portions of the tray may hinder atmospheric air from reaching the surface of the sealant layer as the sealant is curing. As a consequence, the resultant cured sealant layer that is formed on the patient's teeth may be harder and more durable than might otherwise have been formed.

Further details of the invention are defined in the features of the claims.

BRIEF DESCRIPTION OF THE DRAWINGS

FIG. 20 is a perspective view looking toward the top of a tray molding vessel that is adapted to receive a quantity of a second matrix material;

FIG. 21 is a view of the dental arch model shown in FIG. 19 along with the occlusal stop member after the model has been inverted and placed into the vessel of FIG. 20 containing the second matrix material;

FIG. 22 is a cross-sectional view taken in a reference plane lying perpendicular to the curved longitudinal axis of the dental arch model, showing one of the appliances bonded to one of the model teeth and additionally showing the first matrix material, second matrix material and occlusal stop member that together comprise the indirect bonding tray;

DEFINITIONS

Figure 1:
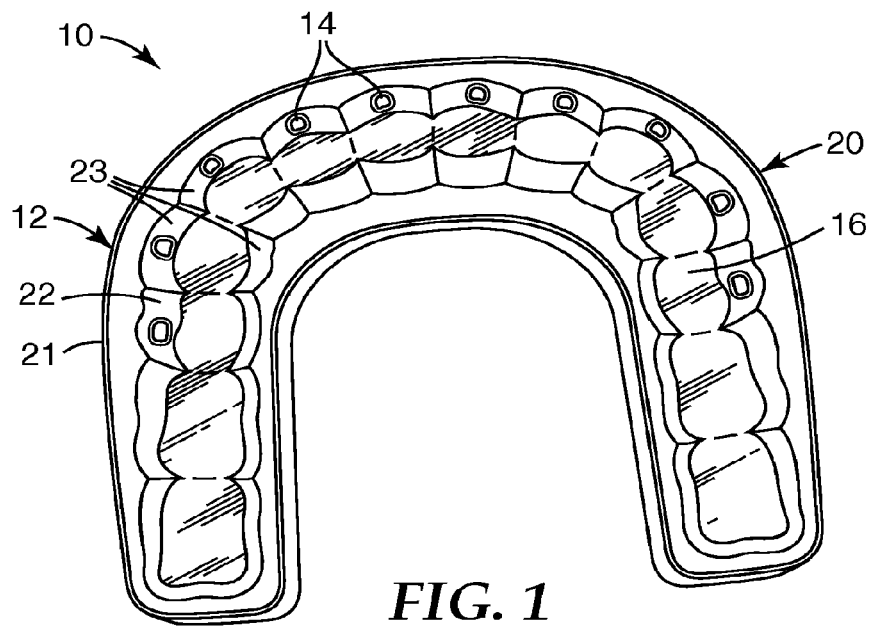
FIG. 1 is a perspective view of orthodontic treatment apparatus constructed in accordance with one embodiment of the present invention, showing an indirect bonding tray, a set of orthodontic appliances that are releasably connected to the bonding tray and a quantity of dental sealant that has been applied to inner wall portions of the bonding tray.

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION OF THE PREFERRED EMBODIMENTS

An orthodontic treatment apparatus for use in carrying out orthodontic therapy according to one embodiment of the invention is illustrated in FIGS. 1-4 and is broadly designated by the numeral 10. The treatment apparatus 10 includes an indirect bonding tray 12, a set of orthodontic appliances 14 releasably connected to the bonding tray 12 along with a quantity of a dental sealant 16 that extends across portions of the bonding tray 12.

Figure 2:
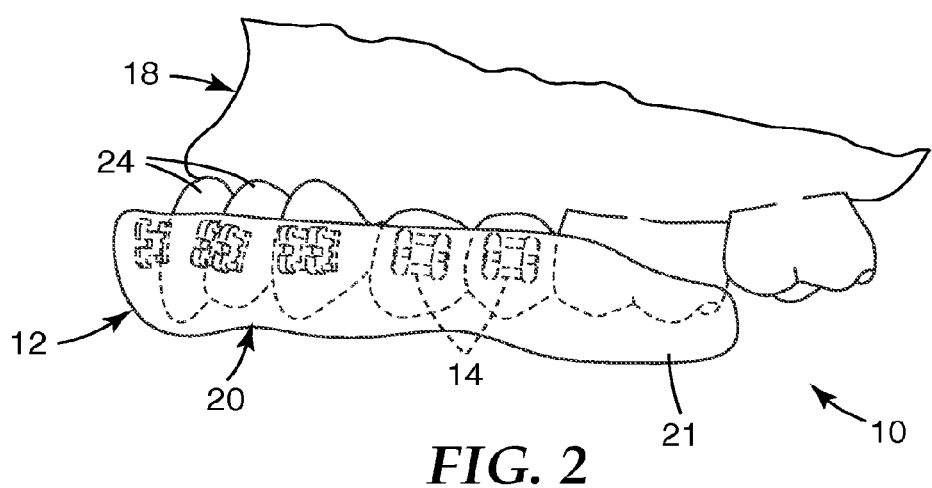
FIG. 2 is an inverted side elevational view of the orthodontic treatment apparatus shown in FIG. 1, and illustrating the indirect bonding tray as it might appear when placed on an upper dental arch of an orthodontic patient.

In the illustrated embodiment, the bonding tray 12 is adapted to fit over a substantial portion of a dental arch of an orthodontic patient, such as the entire upper dental arch 18 shown in FIG. 2 with the exception of the second molar tooth. However, other embodiments are also possible. For example, the bonding tray 12 could be constructed to fit over a smaller number of teeth of a dental arch, such as a left or right quadrant, or only over the non-molar teeth. Alternatively, the bonding tray 12 may be adapted to fit over the patient's lower dental arch or a portion of the patient's lower dental arch.

Figure 3:
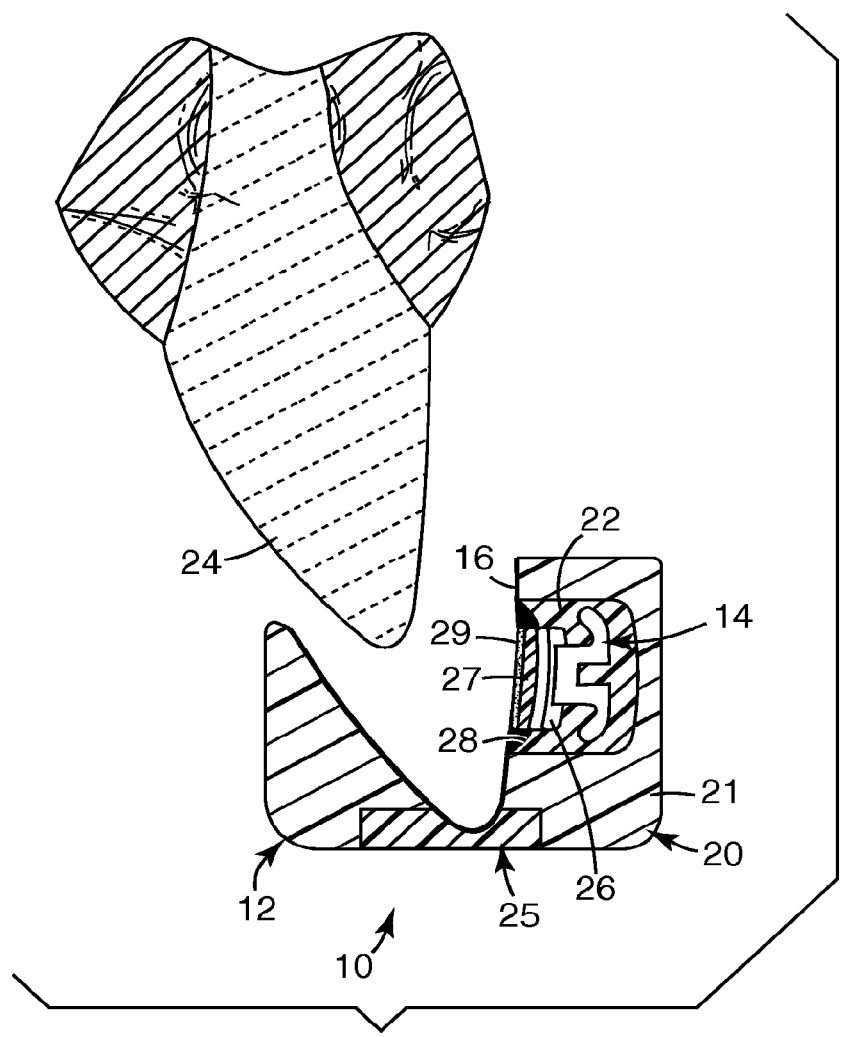
FIG. 3 is an enlarged, exploded, cross-sectional view of the orthodontic treatment apparatus and dental arch depicted in FIG. 2, taken along a reference plane through the upper lateral tooth shown in FIG. 2.

The indirect bonding tray 12 includes a body 20 having an overall, generally U-shaped configuration in plan view that generally follows the curved longitudinal axis of the dental arch 18. The body 20 also has a generally U-shaped configuration in cross-sectional views perpendicular to its curved longitudinal axis, as shown in FIG. 3.

The body 20 preferably includes an outer shell 21 and an inner shell 22. Optionally, both of the shells 21, 22 comprise a matrix material that transmits light. The body 20, optionally including portions of both the outer shell 21 and the inner shell 22, has inner wall portions 23 that present a channel. The wall portions 23 have shapes that match the shapes of underlying surfaces of the patient's teeth (such as tooth 24 shown in FIG. 3) and closely fit against the tooth surfaces when the body 20 is placed over the dental arch 18. Due to the relatively complex shape of the teeth and the mating fit between the inner wall portions 23 and the tooth surfaces of the upper dental arch 18, there is essentially no "slop" or relative movement in lateral directions between the body 20 and the upper dental arch 18 once the body 20 is received in place on the dental arch 18.

Optionally, the body 20 includes at least one stop member 25 (see, e.g., FIG. 3) that is made of a relatively stiff material compared with the material used to form inner shell 22. When the indirect bonding tray 12 is placed over the upper dental arch 18, stop member 25 is positioned over occlusal surfaces of at least some of the respective underlying teeth 24 and provides a relatively rigid stop in contrast to the relatively flexible characteristics of the inner shell 22. The stop member 25 facilitates proper, precise positioning of the orthodontic appliances in desired locations on the teeth 24.

Each of the orthodontic appliances 14 is releasably connected to the inner wall portions 23 of the body 20. In the illustrated embodiment, the appliances 14 are orthodontic brackets, although other appliances such as buccal tubes, sheaths, buttons and bondable bite openers are also possible.

The appliances 14 may be made of any suitable material such as metal (e.g., stainless steel), ceramic (e.g., translucent polycrystalline alumina), plastic (e.g., translucent polycarbonate which maybe optionally reinforced with glass fibers) or combinations thereof.

Preferably, each appliance 14 includes a base 26 and a custom-made bonding pad 27 that extends over the base. The bonding pad 27 has a contour that precisely matches the contour of corresponding regions of the patient's tooth 24. The bonding pad 27 may comprise a hardened adhesive material such as a photocurable orthodontic adhesive that is formed over the base 26 of the appliance 14. Suitable methods for making custom bonding pads 27 are set out in U.S. Pat. No. 7,188,421 (Cleary et al.). Other bonding pads are also possible, such as the custom bonding pads described in U.S. Published Patent Application no. 20070015104 (Wiechmann et al.).

The orthodontic appliances 14 are positioned along the inner wall portions 23 in precise, predetermined locations. As a result, when the bonding tray 12 is placed over the dental arch 18, each appliance 14 will be in its precise intended location on the corresponding tooth 24. In this manner, the orthodontic practitioner can accomplish accurate placement of each of the appliances 14 on the teeth 24 within a relatively short period of time.

Figure 4:
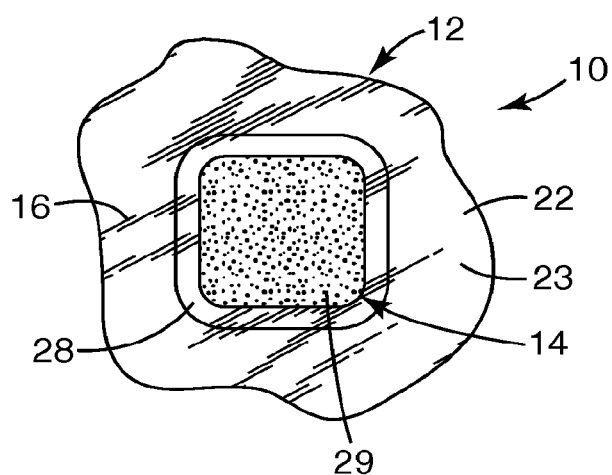
FIG. 4 is an enlarged, fragmentary, side elevational view looking in a facial direction toward a portion of the treatment apparatus shown in FIGS. 1-3.

Preferably, and as illustrated in FIGS. 3 and 4, a groove 28 of the inner wall portions 23 extends along the periphery of each appliance 14. Optionally, each groove 28 circumscribes the base of the corresponding appliance 14 along a path that is closely adjacent the bonding pad 27 of that appliance 14. The groove 28 as shown in FIG. 3 has a transverse cross-sectional shape that generally resembles a sector of a circle, although other cross-sectional shapes are also possible.

The dental sealant 16 extends across at least some of the wall portions 23. Preferably, the sealant 16 extends across an area that surrounds the periphery of each appliance 14 including areas within the grooves 28. Optionally, the dental sealant 16 extends over inner wall portions 23 that correspond to facial, occlusal and lingual regions of the corresponding tooth surfaces. In this manner, the dental sealant 16 can be delivered to a substantial portion if not essentially all of the exposed areas of the patient's teeth once the bonding tray 12 is placed over the dental arch 18.

Advantageously, the grooves 28 serve to collect an accumulation of sealant 16 in areas near the bonding pad 27 of each appliance 14. As a consequence, an increased quantity of sealant 16 will be transferred during a bonding procedure to areas of the patient's teeth adjacent the appliances 14 in comparison to other areas of the teeth. The resultant, thicker sealant layer adjacent the appliances 14 provides additional protection against the formation of white spot lesions and may help seal voids beneath the bonding pad 27 in small areas where a bonding adhesive is lacking.

Suitable dental sealants 16 include ClinPro brand sealant from 3M ESPE and Pro-Seal brand sealant from Reliance Corporation. Color-changing, self-etching compositions may also be used, such as the dental compositions described in pending U.S. Patent Application Ser. No. 60/869,741, filed Dec. 13, 2006. Other suitable dental sealants 16 include curable dental compositions that effectively harden and seal the surfaces of the patient's teeth to hinder formation of plaque. Preferably, the sealant 16 is curable upon exposure to actinic radiation, such as light having wavelengths in the visible range.

An orthodontic bonding adhesive 29 is used for bonding the appliances 14 to the patient's teeth during a bonding procedure. The bonding adhesive 29 extends across the bonding pad 27 of each appliance 14. The bonding adhesive 29 serves in whole or at least in part to securely fix the appliance 14 to the patient's tooth 24 by a bond having sufficient strength to resist unintended detachment from the tooth during the course of treatment.

The bonding adhesive 29 may be a liquid, a semi-liquid, a paste or a solid material that is converted into a liquid, a semi-liquid or paste during the bonding procedure. Suitable adhesives include composites, compomers, glass ionomers and resin-modified glass ionomers. Examples of light-curable adhesives include Transbond XT brand primer, Transbond MIP primer, Transbond XT brand adhesive and Transbond LR brand adhesive from 3M Unitek, and Filtek brand Supreme Plus Flowable adhesive from 3M ESPE. Examples of chemical curing adhesives include Sondhi brand Rapid-Set indirect bonding adhesive, Unite brand adhesive, and Concise brand adhesive from 3M Unitek. An example of an orthodontic bonding adhesive that is both a light-curable adhesive and a chemical curing adhesive is Multi-Cure brand glass ionomer cement from 3M Unitek.

If the bonding adhesive 29 is one component of a two-component bonding adhesive such as the chemical curing adhesives mentioned above, the first and second components advantageously remain out of contact with each other until the practitioner desires to bond the appliance 14 to the patient's tooth 24. Optionally, if one of the components comprises lyophilic ionic cement, the cement may be fixed to the bonding pad 27 by methods described in U.S. Pat. No. 6,050,815 (Adam et al.).

Optionally, the bonding adhesive 29 falls in one of the following classes in accordance with the practitioner's preferences for tooth treatment:

Class I: An adhesive that requires both etching of tooth enamel and a separate application of a primer to the tooth enamel.

Class II: An adhesive that requires etching but not necessarily a separate application of primer.

Class III: An adhesive that requires no treatment of the teeth other than cleaning.

Class I adhesives, which include some chemically cured adhesives, require the use of a suitable etchant such as phosphoric acid or bisphosphonic acid. Possible primers for use with class I adhesives include orthodontic primers such as Transbond MIP brand primer and Transbond XT brand primer from 3M Unitek and Ortho Solo brand primer from Ormco Corporation. Optionally, the primer may include a photobleachable dye to ensure adequate coverage of the primer on the teeth, a small amount of fluoroalumina silicate glass ("FAS" glass) for providing fluoride release during treatment, a small amount of fumed silica for rheology control purposes, and/or a small amount of silanated quartz filler for enhanced fracture toughness.

Suitable class II adhesives, which include many conventionally light cured adhesives, do not require a separate priming step. If the adhesive 29 is a multi-layer adhesive, the adhesive 29 may include a layer of primer that first contacts the tooth during a bonding procedure. As mentioned previously, phosphoric acid or bisphosphonic acid may be used as an etchant. If the adhesive 29 does not include a primer component, the etchant itself may function as a primer. An example of such a self-etching primer is Transbond Plus SEP brand primer from 3M Unitek. Optionally, the self-etching primer could incorporate the optional features described above for the class I adhesive.

Suitable class III adhesives avoid the need for etching and priming the teeth and may be referred to as "self-adhesive" compositions. With these adhesives, the practitioner need only clean the teeth prior to placement of the dental appliance 14 in a typical bonding procedure. Suitable class III adhesives may include an acid component selected from a methacrylate phosphate (e.g., mono-HEMA phosphate, di-HEMA phosphate, glycerol dimethacrylate (GDMA) phosphate), a solution of a bisphosphonic acid in water or other solvent, and a bisphosphonic acid in powder form (using water for ionizing that is left on the teeth after tooth prophy and rinse). Other class III adhesives may include an ethylenically unsaturated component with acid functionality, an ethylenically unsaturated component without acid functionality, an initiator system, and a filler. Optionally a class III adhesive may be essentially free of water. Examples of class III adhesives have been previously described, e.g. in published U.S. Patent Application Nos. 2005/0176844 (Aasen et al.), 2005/0175966 (Falsafi et al.) and 2005/0175965 (Craig et al.).

The class III adhesives described above can optionally incorporate fillers (e.g., a glass ionomer-type filler that binds the water in the usual glass ionomer setting reaction). In addition, any of the class III adhesives described above may incorporate the optional features described in connection with class I adhesives.

Suitable adhesives useful in the present invention may optionally include components such as fluoride releasing agents as described, for example, in U.S. Pat. Nos. 3,814,717 (Wilson et al.) and 6,126,922 (Rozzi et al.); adhesive enhancing agents (e.g., titanates, zirconates) as disclosed, for example, in PCT International Publication No. WO 00/69393 (Brennan et al.); fillers; micro fillers; remineralisation agents; enzyme releasing agents; rheology enhancing agents; photobleachable dyes; thermochromic agents; and combinations thereof. Multi-layer adhesives may also be used, such as described in U.S. Patent Application No. 2005/0136370 (Brennan et al.).

Optionally, the dental sealant and/or the bonding adhesive 29 preferably have an initial color remarkably different than dental structures. Color is preferably imparted to the sealant 16 and/or the adhesive 29 through the use of a photobleachable dye. The sealant 16 and/or adhesive 29 preferably include at least 0.001% by weight photobleachable dye, and more preferably at least 0.002% by weight photobleachable dye, based on the total weight of the sealant 16/adhesive 29. The sealant 16 and/or the adhesive 29 preferably include at most 1% by weight photobleachable dye, and more preferably at most 0.1% by weight photobleachable dye, based on the total weight of the sealant 16/adhesive 29. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, ambient moisture, and the type and weight percent of filler and/or resin. However, the bleaching properties of the dye can be readily determined by irradiating the sealant 16 or adhesive 29 and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof. Reactint dyes may also be used.

The color change in the dental sealant 16 and/or the bonding adhesive 29 is preferably initiated by light. Preferably, the color change is initiated using actinic radiation using, for example, a dental curing light which emits visible or near infrared ("IR") light for a sufficient amount of time. The mechanism that initiates the color change may be separate from or substantially simultaneous with the hardening mechanism that hardens the resin. For example, the sealant 16 and/or adhesive 29 may harden when polymerization is initiated chemically (e.g., redox initiation) or thermally, and the color change from an initial color to a final color may occur subsequent to the hardening process upon exposure to actinic radiation.

The change in sealant and/or adhesive color from an initial color to a final color is preferably quantified by a color test using the L*a*b* system. Using the color test, a value of ΔE* is determined, which indicates the total color change in a 3-dimensional color space. The human eye can detect a color change of approximately 3 ΔE* units in normal lighting conditions. The dental sealant 16 and/or the bonding adhesive 29 is preferably capable of having a color change, ΔE*, of at least 10; more preferably, ΔE* is at least 15; most preferably ΔE* is at least 20.

The L*a*b* system is based on a 3-dimensional color space with the positive X-axis representing red, the negative X-axis representing green, the positive Y-axis representing yellow, the negative Y-axis representing blue, and the Z-axis going from zero (black) to 100 (white) with the origin at 50. ΔE* is a calculation of total color change in the three color dimensions and is described by the following equation:

$$\Delta E^* = \text{Square root}((L_1^* - L_2^*)^2 + (a_1^* - a_2^*) + (b_1^* - b_2^*)^2)$$

where subscript "1" indicates initial state and "2" indicates final state.

Optionally, the manufacturer of the treatment apparatus 10 applies the bonding adhesive 29 to the bonding pad 27 of each appliance 14 before the apparatus 10 is shipped to the practitioner's facility. As another option, or in addition, the manufacturer of the apparatus 10 applies the sealant 16 to the wall portions 23 before the apparatus 10 is shipped to the practitioner's facility. The treatment apparatus 10 is preferably placed in a sealed container by the manufacturer for safe handling and transport to the practitioner's office, where it remains sealed in the container until needed for use.

Figure 5:
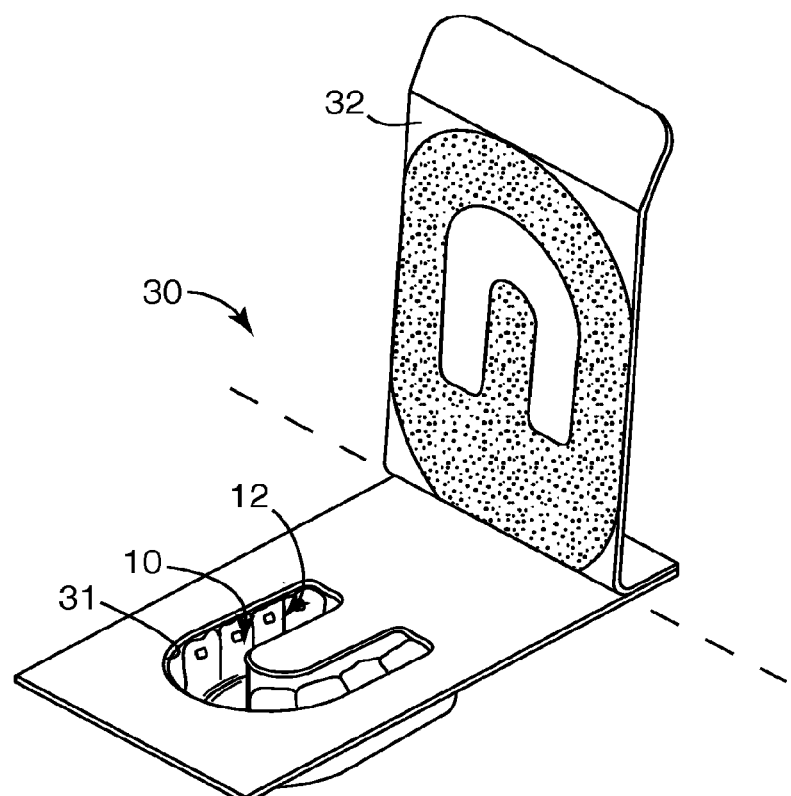
FIG. 5 is a perspective view of orthodontic treatment apparatus according to another embodiment of the invention, wherein the treatment apparatus shown in FIGS. 1-4 has been received in a chamber of a container.
Figure 6:
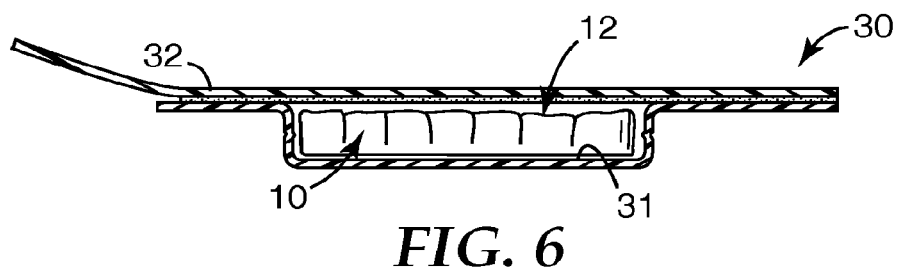
FIG. 6 is a side cross-sectional view of the container and treatment apparatus illustrated in FIG. 5, except that a cover of the container has been closed.

A suitable shipping container 30 for the treatment apparatus 10 is illustrated in FIGS. 5 and 6. The container 30 includes a substrate with a chamber 31 for receiving the apparatus 10. A cover 32 of the container 30 is movable between a closed position as shown in FIG. 6 wherein the cover 32 extends across the chamber 31 and an open position as shown in FIG. 5 wherein the cover 32 is spaced apart from the chamber 31.

In the example shown in FIGS. 5 and 6, the substrate of the container 30 includes a generally U-shaped bottom wall and an upright side wall, both of which present a generally U-shaped configuration in top view. A rectangular top flange of the substrate surrounds an opening to the chamber 31 and is integrally connected to the side wall of the substrate. A pressure sensitive adhesive extends across portions of the cover 32 and engages the top flange for releasably retaining the cover 32 in the closed position and in contact with the substrate. Other constructions are also possible.

In embodiments of the invention wherein the dental sealant 16 and the bonding adhesive 29 are applied to the wall portions 23 and the appliances 14 respectively by the manufacturer of the apparatus 10, the container 30 serves to protect the dental sealant 16 and the unhardened bonding adhesive 29 from contaminants such as dust, moisture and the like. In addition, the container 30 including the cover 32 is constructed to avoid deterioration of the adhesive characteristics of the bonding adhesive 29, so that the ultimate strength of the bond between the appliances 14 and the patient's teeth is relatively high. If, for example, the bonding adhesive 29 and/or the dental sealant 16 are curable upon exposure to actinic radiation, the container 30 is constructed of a material that provides a substantial barrier to the transmission of actinic radiation. Suitable materials for the cover 32 and the substrate of the container 30 include flexible plastic materials such as black or red polyethylene-terephthalate glycol (PETG).

Optionally, portions of the container 30 are made of a material that substantially hinders the passage of actinic radiation but enables the passage of light in at least a portion of the visible spectrum so that the presence of the treatment apparatus 10 within the container 30 can be confirmed without opening the cover 32. As another option, the cover 32 may include a layer of paper that is bonded to a barrier layer such as aluminum foil. The barrier layer substantially blocks the passage of volatile components of the bonding adhesive 29. Examples of suitable materials for the container 30 as well as methods for constructing the container 30 are set out in U.S. Pat. Nos. 5,538,129 and 5,354,199 as well as published U.S. Patent Application No. 2003/0196914.

Alternatively, the container 30 may include a hermetic seal in regions between the flange of the container 30 and the cover 32 instead of the pressure sensitive adhesive described above. The use of a hermetic seal helps to prevent volatile components of the bonding adhesive 29 and/or the dental sealant 16 from contacting a pressure sensitive adhesive such as the pressure sensitive adhesive on the cover 32 as described above. As a result, the hermetic seal decreases the loss of volatile components from within the chamber 31. As yet another option, both a hermetic seal and a pressure sensitive adhesive may be provided.

As a further option, the container 30 may be provided with an additional quantity of one or more components of the bonding adhesive 29 and/or dental sealant 16 that are volatile, to help decrease the loss of such volatile components. For example, the bonding adhesive 29 may contain ethyl 4-dimethylaminobenzoate ("EDMAB") and/or camphorquinone ("CPQ") both of which may volatilize over a period of time after the container 30 is closed. By adding an additional quantity of such components in the chamber 31, equilibrium is shifted and there is less likelihood of losing an undue quantity of such components from the bonding adhesive 29 or dental sealant 16. As a result, there is less likelihood that the characteristics of the bonding adhesive 29 or the dental sealant 16 are impaired over a period of time. The additional volatile components may be provided in a liquid that is placed in a well adjoining the chamber 31, or may be placed in a porous material (such as a sponge or fabric) that optionally serves as a packing material for the treatment apparatus 10.

Preferably, the container 30 is constructed so that the cover 32 is self-retained in the open position as illustrated in FIG. 5 once the container 30 has been opened. To this end, the cover 32 may be provided with a line of weakness such as a series of perforations that extend along the axis that is designated by the dashed line in FIG. 4. In addition to helping retain the cover 32 in an open orientation, the perforations also provide tactile feedback to the user that the cover 32 has opened so that the user does not continue to pull on the cover 32 and separate the same from the flange of the substrate.

Figure 7:
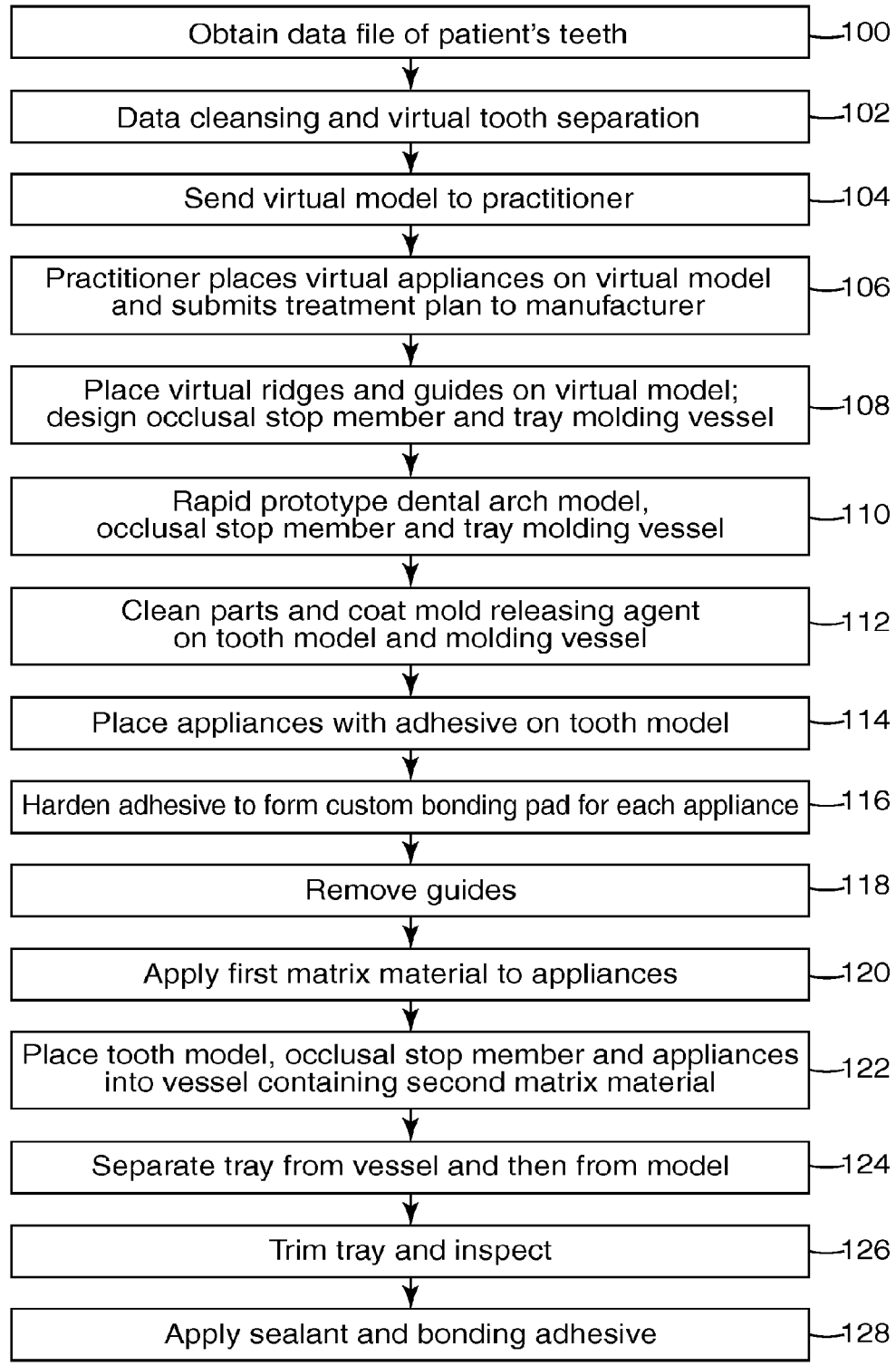
FIG. 7 is a block diagram describing some of the steps that are followed in making an orthodontic treatment apparatus according to one embodiment of the invention.

FIG. 7 is a block diagram describing some of the steps that are carried out in one method of making the treatment apparatus 10, although other methods are also possible. Block 100 represents the step of obtaining a digital data file of the patient's teeth and optionally the patient's adjacent gingival tissue. The digital data may be obtained by the use of a hand-held intra-oral scanner such as the intra-oral scanner using active wavefront sampling developed by Brontes Technologies, Inc. Alternatively, other intra-oral scanners or intra-oral contact probes may be used. As another option, the digital data file may be obtained by scanning an impression of the patient's teeth. As still another option, the digital data may be obtained by scanning the physical model of the patient's teeth or by using a contact probe on a model of the patient's teeth. The model used for scanning or for contact probing may be made by pouring a casting material (such as plaster of Paris or epoxy resin) into an impression of the patient's teeth and allowing the casting material to cure. Any suitable scanning technique may be used for scanning the model, such as X-ray, laser, light-based scanning, computed tomography (CT), and magnetic resonance imaging.

In block 102, the digital data file of the patient's teeth obtained in block 100 is "cleansed" by removing any data points that represent clear error. For example, STL files representing a tooth surface that include a data point significantly outside the normal expected geometrical relationship of adjacent data points could be fixed by STL-handling software to remove the erroneous data point. In addition, tooth data points that are missing could be added by STL-handling software to create realistic, smoothly curved tooth shapes. Alternatively, or in addition to, the data cleansing may be carried out on the data file before conversion of the data to an STL file.

As an additional option, data may also be obtained of hidden features of the patient, such as the roots of the patient's teeth and the jaw structure. For example, CT scanning techniques may be used to obtain data representative of the patient's entire tooth structure including the roots. The data obtained by CT scanning may then be "stitched together" with other data obtained by scanning the crowns of the patient's teeth with another scanning technique so that the practitioner may ultimately obtain a better understanding of tooth movement during the course of treatment.

As also represented by block 102, the digital data file of the patient's dental arch is then modified to provide virtual separation of each tooth from adjacent teeth and gingiva so that each tooth may be independently moved as a separate object. Next, and as represented by block 104, the modified virtual model is forwarded to the practitioner. For example, if the steps in block 102 are carried out at a manufacturing facility, the facility may send the virtual model to the practitioner over a wired communications network such as the internet. The practitioner then interacts with a local computer to view the three dimensional ("3D") virtual model and determine the desired final positions of the patient's teeth.

As shown in block 106, the practitioner selects and places virtual appliances such as brackets and buccal tubes on the virtual model using the local computer. During this process, the practitioner selects virtual appliances that embody certain geometric attributes and also selects the positions of the appliances on the patient's teeth within the modeling environment. The modeling software manipulates each bracket and each tooth as a separate object within the 3D environment and fixes the position of each bracket within the 3D space relative to a coordinate system associated with the tooth of the corresponding bracket. The modeling software then computes the final positions of the teeth based on the positions of the appliances selected by the practitioner and displays the virtual teeth in their final occlusion.

If the practitioner is not entirely satisfied with the final predicted positions of the teeth, the practitioner may use the modeling software to move one or more of the virtual appliances relative to the virtual teeth. The modeling software will then compute and display new final positions of the virtual teeth based on the revised positions of the virtual appliances on the virtual teeth. These steps can be repeated as many times as desired until the practitioner is satisfied with the final positions of the virtual teeth as represented by the modeling software. As an alternative to moving appliances, however, the practitioner may use the modeling software to move the virtual teeth to desired positions, and the modeling software will then compute positions of the appliances on the teeth for moving the teeth to those desired positions. Data representing the selected positions of the appliances, along with identification data for each appliance (such as brand name and the manufacturer's part number), tooth identification data (such as tooth type and location in the oral cavity) and patient data (such as name and birth date, or a patient identification number) is then submitted to the manufacturing facility.

Optionally, the local computer at the practitioner's office or a remote computer accessed through the internet may include subprograms suitable to analyze the existing malocclusion of the patient and assist in determining the desired ultimate positions of the appliances on the patient's teeth. The software may also include subprograms to assist in suggesting or selecting the proper appliances for treatment of the particular malocclusion at hand.

As yet another option, the steps in block 106 may be carried out by a technician at a location remote from the practitioner's office. For example, a technician at the manufacturer's facility may use software to place virtual appliances on the virtual dental model in accordance with known standards in the art or in accordance with general guidelines previously provided by the practitioner. Once the technician is satisfied with the appliance positions and the resulting finished positions of the teeth, the virtual model together with the data representing the appliance positions is forwarded to the practitioner for review. The practitioner can then either approve the technician's appliance placement positions or reposition the appliances as desired. The practitioner then forwards the virtual model together with the appliance tooth and patient data as mentioned above back to the manufacturer.

Block 108 describes steps that are preferably undertaken at the manufacturer's facility using data of the virtual dental model and identification data of the appliances and position data of the appliances. Ridges for circumscribing the base of each appliance on a physical model are first created by creating virtual ridges corresponding to the shape of the periphery of each appliance base. The virtual ridges are created on the virtual model using software. Next, alignment structure for use in placing appliances on a physical model is created by first creating one or more virtual guides on the virtual model using software. Preferably, virtual guides are created corresponding to each appliance and are connected to the virtual ridge for the associated appliance. In addition, one or more occlusal stop members are designed and the shape of a tray molding vessel is determined. A data file of the virtual model with the ridges and guides, a data file of the occlusal stop member and a data file of the tray molding vessel are then forwarded to a rapid prototyping machine as described in block 110. The occlusal stop member and the tray molding vessel are described in more detail below.

As used herein, rapid prototyping is the process of generating an object directly from digital data, such as digital data representing its shape. Examples of suitable rapid prototyping processes include solid freeform fabrication such as 3D printing processes, stereolithography methods, fused deposition modeling, laminated object manufacturing, laser engineered net shaping, selective laser sintering, shape deposition manufacturing and solid ground curing. An example of a suitable 3D printing machine is the Eden brand 500V printer from Objet Geometries Ltd., using FullCure 720 acrylic-based photopolymer printing material (also from Objet Geometries Ltd.). Another example of rapid prototyping is the use of CAD-CAM software to direct a milling machine to mill the dental arch model with the ridges and alignment guides, the occlusal stop member and the tray molding vessel. The manufactured parts are then cleaned as described in block 112.

Figure 8:
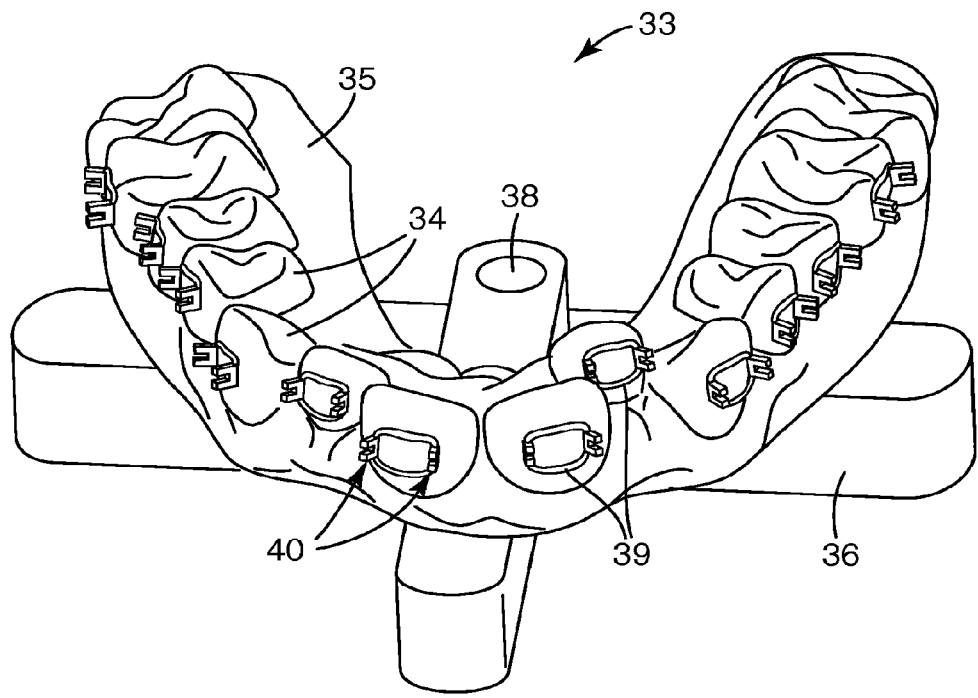
FIG. 8 is a perspective view showing a model of a patient's dental arch as described in FIG. 7, looking in directions toward facial and occlusal surfaces of the arch model and additionally showing a substrate of the arch model.

An exemplary dental arch model 33 made by rapid prototyping is illustrated in FIG. 8. In this embodiment, the arch model 33 includes a portion of the model gingival tissue 35 as well as individual model teeth 34. The arch model 33 as shown represents the patient's entire upper dental arch, and preferably a model of the patient's lower dental arch (not shown) is also provided. Alternatively, the arch model may include only a portion of the arch (for example, an arch quadrant) in instances where the resulting indirect bonding tray is to be used to bond appliances to only a portion of the patient's dental arch. Optionally, when the arch model 33 is made using a 3D printing machine, the arch model 33 could be hollow to reduce the expense associated with the printing material.

In addition to the model gingival tissue 35 and the model teeth 34, the arch model 33 also includes a pedestal or substrate 36. In this embodiment, the substrate 36 has the shape of a cross and includes alignment structure comprising two holes 38 (only one is numbered), the purpose of which will be explained below. However, the substrate 36 may be constructed in other shapes as well, such as a generally circular-shaped disk that extends along the base of the model gingival tissue 35. Preferably, the arch model 33 is printed as a single, unitary component such that the substrate 36 is integrally connected with the model gingival tissue 35.

The ridges and guides as mentioned in block 108 preferably include one or more ridges and guides associated with each appliance and its corresponding model tooth 34. In the embodiment shown in FIGS. 8-11 and 14-16, two guides 40 are integrally connected to each ridge 39 of each corresponding model tooth 34 as a consequence of being simultaneously fabricated by rapid prototyping during rapid prototyping of the arch model 33. Each ridge 39 (shown by dotted lines in FIGS. 9-11) extends in a closed-loop path that surrounds the intended location of the bonding pad 27 of the corresponding appliance 14. Each of the guides 40 includes a generally U-shaped body 42 (see, e.g., FIGS. 9 and 11) with a channel 44 defined by occlusal, lingual and gingival walls that are optionally flat.

Figure 9:
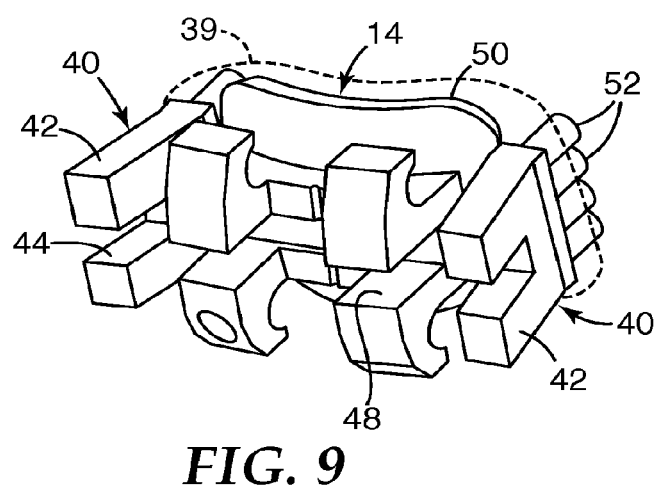
FIG. 9 is an enlarged perspective view showing an exemplary ridge and exemplary alignment guides of the dental arch model illustrated in FIG. 8 along with the orthodontic appliance as it might appear when the appliance is placed on the model, and looking in a direction toward the facial and occlusal surfaces of the appliance.
Figure 10:
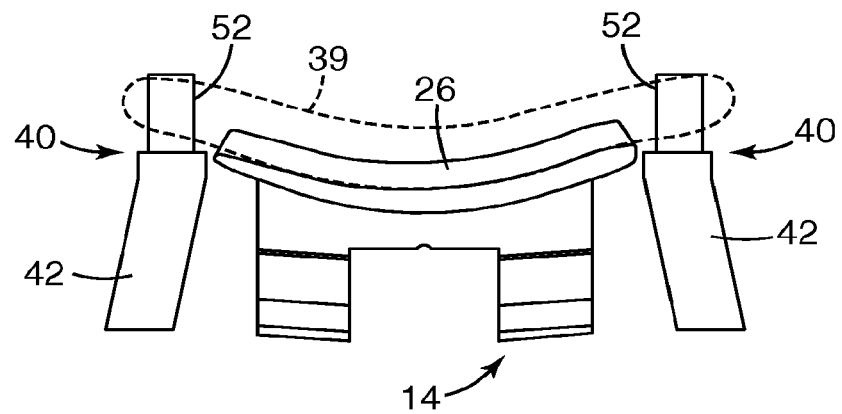
FIG. 10 is a top view of the ridge, guides and appliance shown in FIG. 9, looking in a direction toward the occlusal surfaces of the appliance.
Figure 11:
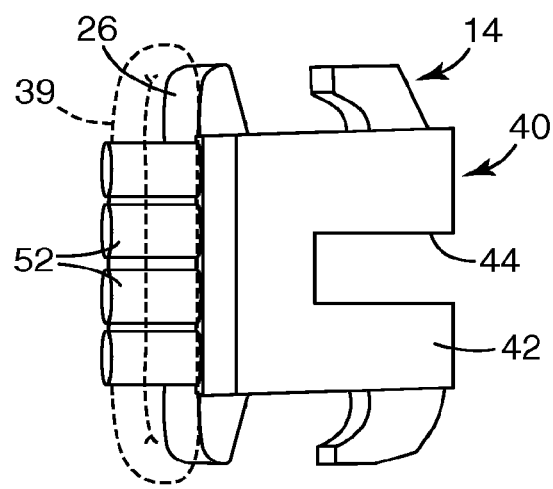
FIG. 11 is a side view of the ridge, guides and appliance shown in FIGS. 9 and 10, looking in a direction toward a distal side of the appliance.

The exemplary orthodontic bracket appliance 14 shown in FIG. 3 is also depicted in FIGS. 9-11. The appliance 14 is received in the space between the two guides 40 associated with one of the model teeth 34 such that the base 26 of the appliance 14 is surrounded by the ridge 39. The appliance 14 has an archwire slot 48 (FIG. 9) adapted to matingly receive an archwire. In the example shown in the drawings, the appliance 14 is known as a twin tiewing bracket and optionally includes a hook (not shown).

The guides 40 each have a known physical characteristic relative to a structural feature of the corresponding appliance 14, such as the archwire slot 48. In the illustrated embodiment, the known physical characteristic of the guides 40 includes the orientation of the three walls defining the channel 44. For example, and in this embodiment, the occlusal, lingual (or bottom) and gingival walls of the channel 44 of each guide 40 are coplanar with the occlusal, lingual and gingival walls respectively of the archwire slot 48 when the appliance 14 is properly positioned on the model tooth 34 and between the guides 40.

However, alternative constructions are also possible. For example, the three walls of the channel 44 could extend in reference planes that are offset but parallel to the respective three walls defining the archwire slot 48. As yet another example, the three walls of the channel 44 of each guide 40 may be oriented at an angle relative to the respective three walls of the archwire slot 48.

As another alternative construction, the guides 40 could be located along occlusal and gingival sides of the appliances, or along any other combination of two sides. Moreover, the height of the guides 40 may be reduced to avoid interference with the guides 40 or appliances 14 associated with adjacent teeth, and optionally the distance of the lingual wall of the channel 44 from the adjacent surface of the model tooth 34 could be less than the distance of the lingual wall of the archwire slot 48 from the model tooth 34 when the appliance 14 is in its intended position. In these instances, the construction of the appliance holder as described below is revised as necessary to facilitate use of the holder with such guides 40.

Preferably, the guides 40 as shown in FIGS. 9-11 are spaced apart from each other a distance in a mesial-distal direction that is only slightly larger than the overall, mesial-distal width of the base 26 of the appliance 14. However, to facilitate insertion of the appliance 14 in the space between the guides 40, the guides 40 preferably extend at an angle away from each other as the outer ends of the guides 40 are approached as can be appreciated, for example, by reference to FIG. 10. In FIG. 10, the combined angle between the inner, facing walls of the two guides 40 is approximately 10 degrees, although other angles are also possible.

Each of the guides 40 is preferably connected by detachable structure to the ridge 39 of the associated model tooth 34. In the embodiment shown in FIGS. 9-11, each of the guides 40 include four cylindrical legs 52 that integrally connect the body 42 to the associated ridge 39. The legs 52 can be readily fractured by urging the associated body 42 in a direction away from the appliance 14 using a pivotal, swinging motion in order to detach and separate the guide 40 from the ridge 39 when desired.

Figure 12:
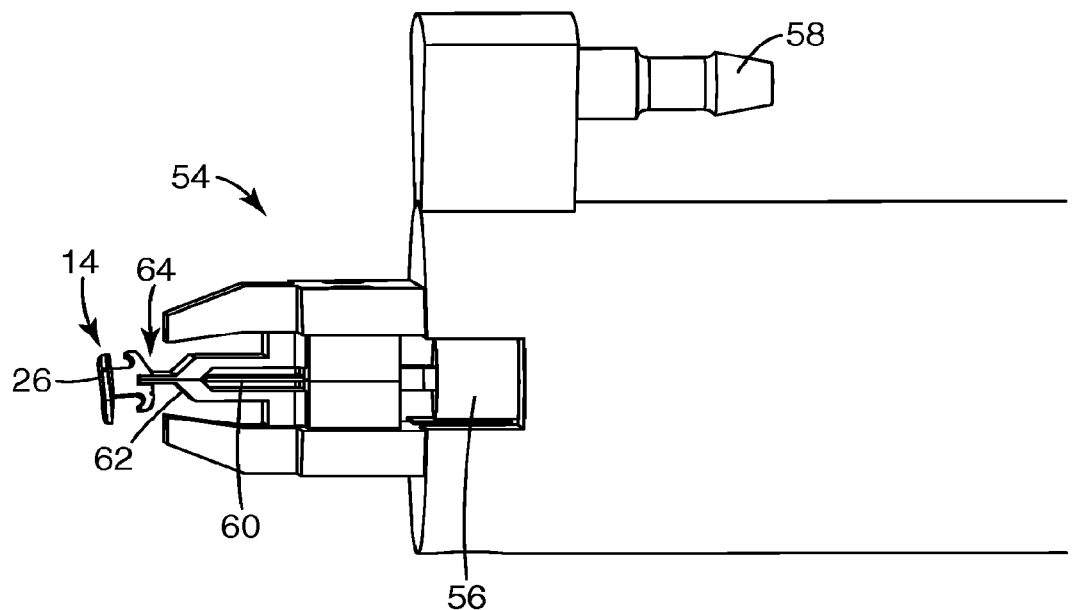
FIG. 12 is a fragmentary perspective view of one type of holder that may be used for placing appliances on the model, wherein the holder includes a gauge that is received in an archwire slot of the appliance.
Figure 13:
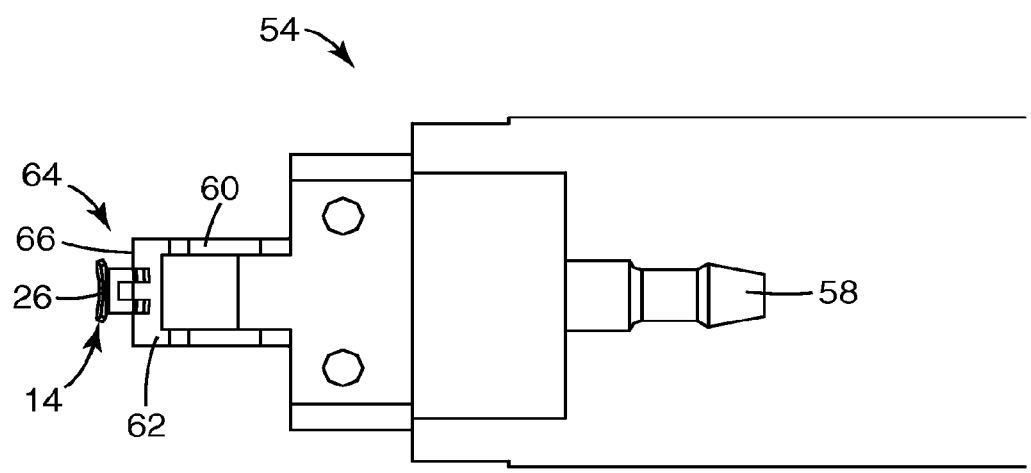
FIG. 13 is a fragmentary view somewhat similar to FIG. 12 except looking in a direction toward the top of the holder and an occlusal side of the appliance.
Figure 14:
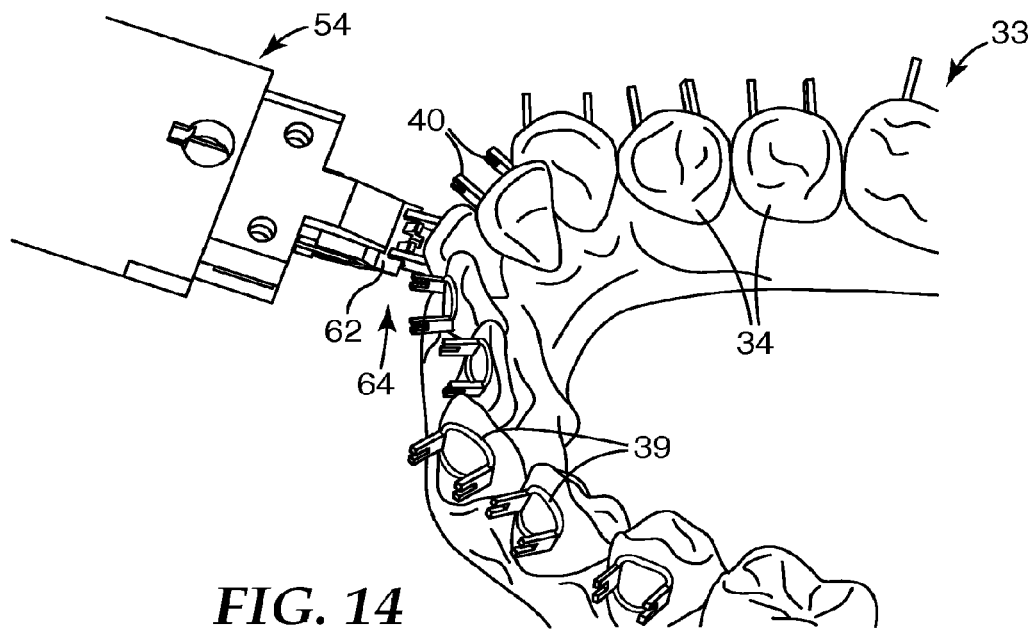
FIG. 14 is a fragmentary perspective view showing an exemplary use of the holder illustrated in FIGS. 12 and 13 in placing the appliance on the dental arch model shown in FIG. 8.

FIGS. 12-14 illustrate an exemplary holder 54 that may be used to position and place the appliances 14 onto the dental arch model 33. The holder 54 includes an air-operated piston and cylinder assembly 56 (FIG. 12) that receives air for actuation of the piston through inlet 58. The piston of the assembly 56 is connected to a blade expander 60 that is positioned between two resilient gripper blades 62. The two blades 62 together represent a placement gauge 64, and serve to releasably hold the appliance 14 as well as to guide the appliance 14 to a proper position by use of a releasable, mating fit with the guides 40.

The gripper blades 62 of the holder 54 have outer portions that converge toward each other and then continue in parallel planes to outer ends 66 (see, e.g., FIG. 13). As air is directed to the piston and cylinder assembly 56, the piston extends and moves the blade expander 60 toward the converging portions of the blades 62 to move, in turn, the outer ends 66 in directions away from each other. As the outer ends 66 move away from each other, they come into secure contact with occlusal and gingival walls of the archwire slot 48 and thereby serve to securely hold the appliance 14 during appliance placement.

Other constructions for the holder 54 are also possible. For example, the holder 54 may include a piezo-electric element, such as a rectangular prismatic bar, that expands in an occlusal-gingival direction when sufficient voltage is applied to the element. As the element expands, it contacts the occlusal and gingival walls of the archwire slot 48 to securely grip the appliance 14. In this manner, the appliance 14 can be gripped or released on demand by operation of an electric switch that could be placed on a handle of the holder or in a remote location such as a foot pedal.

Once the appliance 14 is gripped by the outer ends 66 of the holder 54, the appliance 14 is placed between guides 40 of the alignment structure in order to temporarily bond the appliance 14 to the associated model tooth 34 as described in block 114. However, before placement of the appliances 14 on the dental arch model 33, a release agent is applied to the model teeth 34 and model gingival tissue 35 as described in block 112. An example of a suitable release agent is water soluble polyvinyl alcohol, such as "PA0810" from PTM&W Company of Santa Fe Springs, Calif.

A bonding composition (not shown in FIGS. 12-14) for making the bonding pads 27 is placed between the base 26 of each appliance 14 and the associated model tooth 34. Preferably, the bonding composition is a light-curable composition such as a light curable adhesive, and the adhesive is coated across the base 26 of each appliance 14. Optionally, the appliances 14 are adhesive precoated appliances that have a layer of light-curable adhesive applied by the manufacturer to the base 26 of each appliance 14, such as APC Plus brand appliances and APC II brand appliances from 3M Unitek Corporation. Examples of adhesive coated appliances are described in U.S. Pat. Nos. 5,015,180, 5,172,809, 5,354,199, 5,429,229, 6,183,249 and 6,960,079.

If the appliances 14 are not coated with adhesive in advance by the appliance manufacturer, the bonding composition is applied to the base 26 of each appliance 14 immediately before placement of the appliance 14 on the arch model 33. Suitable bonding compositions include orthodontic adhesives such as composites, compomers, glass ionomers and resin-modified glass ionomers, including the class I, class II and class III adhesives described above in connection with the bonding adhesive 29. Examples of light-curable adhesives include Transbond XT brand and Transbond LR brand adhesives from 3M Unitek Corporation. Examples of chemical curing adhesives include Concise brand adhesive and Multi-Cure brand glass ionomer cement from 3M Unitek Corporation.

As the appliance 14 is moved toward the guides 40, the outer ends 66 of the holder 54 move into the channel 44 of each body 42. The holder 54 continues to move toward the arch model 33 until such time as the outer ends 66 have seated against the lingual wall of the channels 44. Preferably, the distance between the occlusal and gingival walls of the channel 44 of each body 42 is only slightly larger than the distance between the occlusal and gingival walls of the archwire slot 48 so that the outer ends 66 are matingly received in the channel 44 without undue possible lateral movement or "slop". An example of a suitable tolerance or difference between such distances is plus or minus 0.1 mm.

When the appliance 14 is properly oriented relative to the guides 40, the three walls of the archwire slot 48 have an orientation in 3D space that is coplanar with the respective three walls of the channel 44 of each guide 40, such that the guides 40 have known physical characteristics relative to the appliance 14. Since the outer ends 66 of the holder 54 when fully expanded against the occlusal and gingival walls of the archwire slot 48 have a known physical characteristic relative to the appliance 14 (in this embodiment, known orientations in 3D space relative to the archwire slot 48) as well as a known physical characteristic relative to the guides 40 (in this embodiment, known orientations in 3D space relative to the channels 44), the holder 54 accurately places the appliances 14 relative to the guides 40 with high precision. In addition, since the software used to design the virtual ridges and virtual guides is able to orient the virtual guides in precise, desired positions relative to the associated virtual tooth, the model guides 40 as produced by rapid prototyping are accurately oriented relative to the desired position of the associated appliances 14 on the model teeth 34. Furthermore, since the orientation of the ridges 39 and guides 40 is determined by the orientation of the associated appliance 14, the software can change the orientation of the ridges 39 and guides 40 if the desired position of the appliance 14 is changed.

Additionally, the guides 40 can be designed by the software to support the appliance 14 in one or more angular orientations that may deviate from a typical orientation of the appliance 14 relative to the associated tooth 34. As an example, the guides 40 can be designed to provide supplemental tip and/or torque (i.e., tip and/or torque that differs from the amount of tip and/or torque that is provided by the appliance 14) by orienting the channels 44 in appropriate directions. Optionally, the guides 40 can be designed to orient and support the base 26 of the appliance 14 in an angular orientation such that the base 26 is not uniformly spaced from the adjacent tooth surface of the model tooth 34 and the thickness of the bonding composition used to make the bonding pad 27 varies. For example, the guides 40 could be constructed to enable the resulting bonding pad 27 to be thicker along the mesial side of the base 26 as compared to the distal side of the base 26 so that the associated tooth of the patient will tend to be rotated about its long axis during the course of treatment.

Preferably, the software automates the design of the ridges 39 and guides 40 by reference to geometric parameters particular to the selected appliances 14. For example, a database containing information for each appliance 14 such as its mesial-distal width, in-out dimension, torque and angulation can be established, and the software can design the ridges 39 and guides 40 based on design templates and information in the database.

Other constructions for the holder 54 are also possible. For example, opposite sides of the outer end 66 of the holder 54 may be stepped and/or oriented at an angle in correspondence with a stepped shape and/or orientation of the guides 40 as mentioned earlier. In addition, opposite sides of the outer ends 66 may include features that engage structure of the ridge 39, guides 40 and/or the appliance 14 to provide proper orientation of the appliance 14 in a mesial-distal direction. In instances where the latter option is used, the guides 40 may be spaced further apart from each other and need not contact the base 26 of the appliance 14 for mesial-distal positioning. As one example, the outer ends 66 may include a protrusion that is adapted for snug, mating reception in the occlusal-gingival or "vertical" channel that is located between mesial and distal tiewings of a twin tiewing bracket.

Once the outer ends 66 of the holder 54 are firmly seated in the channels 44 of the guides 40, the piston of the piston and cylinder assembly 56 is retracted to shift the blade expander 60 in a direction away from the outer tip portions of the gripper blades 62. As the blade expander retracts, the resilient gripper blades 62 (preferably made of tool steel) self-move toward each other such that the outer ends 66 no longer tightly engage the occlusal and gingival walls of the archwire slot 48. The holder 54 can then be moved in a direction away from the appliance 14 to detach the outer ends 66 from the archwire slot 48.

Next, the bonding composition is allowed to harden and form the custom bonding pad 27 for the base 26 as described in block 116. The resulting bonding pad 27 is advantageous in that it has a contour that precisely matches the contour of the model tooth 34 and hence matches the contour of the respective tooth 24 of the patient. This matching shape facilitates the subsequent bond of the appliance 14 to the patient's tooth 24 and reduces the likelihood that the appliance 14 will unintentionally detach from the tooth 24 during the course of treatment.

Figure 15:
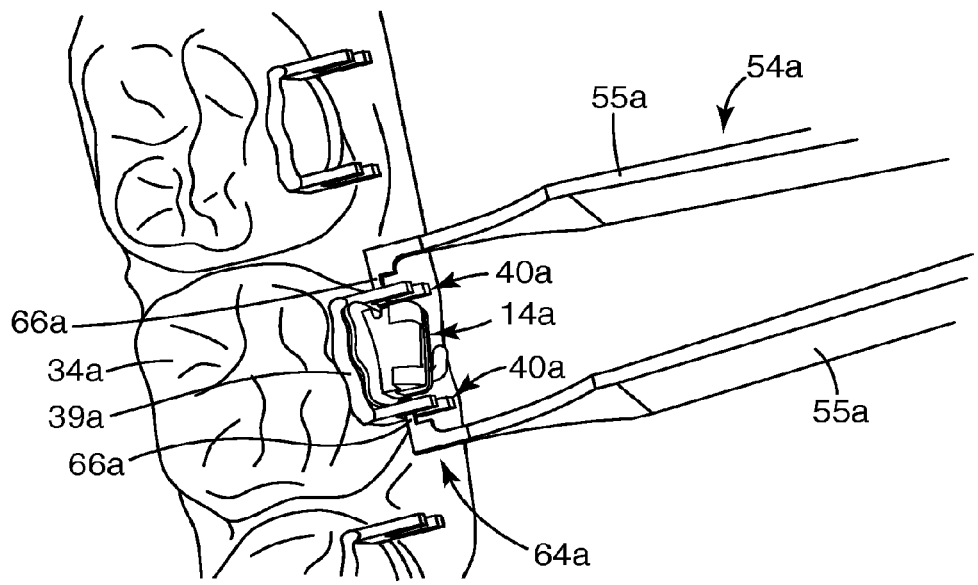
FIG. 15 is a fragmentary perspective view of an alternative holder for placing orthodontic appliances on the dental arch model, wherein the holder is particularly useful for placing appliances that have a closed archwire slot such as buccal tubes.

An orthodontic appliance holder 54a according to another construction is illustrated in FIG. 15 and is particularly useful in connection with the placement of orthodontic appliances that have an archwire slot that is closed along its labial side. Examples of such appliances include buccal tubes, which have an archwire slot that resembles an elongated passage. This passage has open mesial and distal ends and often has a rectangular shape in cross-sectional view. An exemplary buccal tube appliance 14a is also shown in FIG. 15.

The holder 54a includes a pair of arms 55a, each of which includes an outer, generally "L"-shaped end portion that terminates at an outer end 66a. The opposed outer ends 66a extend toward each other and have a rectangular cross-sectional shape that is constructed for mating reception into a rectangular passage of buccal tube appliance 14a. The outer ends 66a collectively represent a gauge 64a for aligning and placing the buccal tube appliance 14a in its proper position on the corresponding model tooth 34a.

The arms 55a are movable by finger pressure in directions toward each other, and sufficiently resilient to self-move away from each other when finger pressure is relieved. When in a relaxed orientation, the arms 55a are sufficiently spaced from each other such that the distance between the facing tips of the outer ends 66a is greater than the overall distance between the mesial and distal openings of the archwire slot of the buccal tube appliance 14a. When it is desired to place the buccal tube appliance 14a on the model tooth 34a, the user guides the outer ends 66a to respective positions adjacent the mesial and distal openings of the archwire slot of the buccal tube appliance 14a, and then applies pressure to the arms 55a to urge the arms 55a together. As the outer ends 66a move toward each other, the outer ends 66a slide into the archwire slot of the buccal tube appliance 14a so that the latter can be manipulated as needed. The matching rectangular cross-sectional shapes of the outer ends 66a and the archwire slot of the appliance 14a ensures that the appliance 14a does not rotate about the longitudinal axis of the archwire slot during such movement and placement.

As shown in FIG. 15, a pair of spaced apart guides 40a is integrally connected to a loop-shaped ridge 39a provided on the model molar tooth 34a. The guides 40a are similar to the guides 40 in that the guides 40a each have a channel with occlusal, lingual and gingival walls. These occlusal, lingual and gingival walls are designed and constructed to be oriented in co-planar relation with the occlusal, lingual and gingival walls respectively of the archwire slot of the buccal tube appliance 14a when the buccal tube appliance 14a is in its desired orientation on the model tooth 34a.

During placement of the appliance 14a, the outer ends 66a of the holder 54a are received in the channels of the guides 40a. The appliance 14a is moved in a lingual direction toward the model tooth 34a until the outer ends 66a contact the bottom or lingual wall of the channels of the guides 40a. Once this contact is established, pressure on the arms 55a is released and the arms 55a spread open. As the arms 55a move away from each other, the outer ends 66a move out of the archwire slot of the appliance 14a, and thus enable the holder 54a to be moved away from the model tooth 34a without disturbing the position of the appliance 14a.

The use of the appliance holders 54, 54a in combination with guides 40, 40a has been described above as a manual procedure that is easily carried out by hand. Alternatively, however, the appliance holders 54, 54a may be adapted for use with automated robotic machinery for grasping the appliances 14, 14a and placing the same on the arch model 33. Software programmed for the robotic machinery can provide instructions to retrieve each appliance 14, 14a from a designated storage location for appliances 14, 14a in inventory such as a rack system that holds the appliances 14, 14a in a known orientation. Once the robotic machinery has moved the holder 54, 54a coupled to the machinery to retrieve an appliance 14, 14a from inventory, the robotic machinery maneuvers the holder 54, 54a to move the appliance 14, 14a into a position so that the outer ends 66, 66a of the holder 54, 54a contact the guides 40, 40a.

Although robotic machinery in theory can be operated with great precision to place appliances 14, 14a on model teeth 34, 34a, the use of alignment structure such as guides 40, 40a is an advantage in that small errors in the position of the holder 54, 54a can be tolerated. So long as the robotic machinery provides the holder 54, 54a with sufficient freedom to move small, limited distances during placement of the appliances 14, 14a, the guides 40, 40a can serve to properly position the holder 54, 54a as the appliance 14, 14a is placed on the model teeth 34, 34a. Optionally, the ridges 39, 39a may also be designed with sufficient inclination and height in a labial direction to help guide the respective appliances 14, 14a to proper positions on the model teeth 34, 34a.

Figure 16:
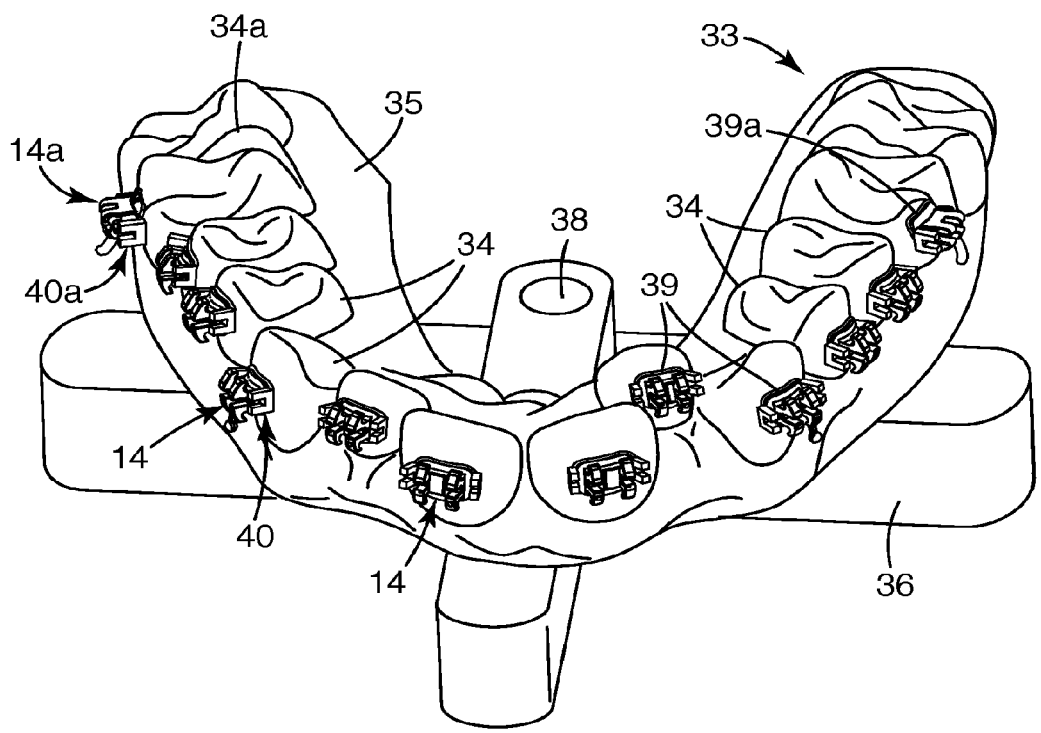
FIG. 16 is a perspective view of the dental arch model shown in FIG. 8 along with a set of orthodontic appliances that have been placed on the dental arch model using the guides.

FIG. 16 is a view somewhat similar to FIG. 8, except in FIG. 16 all of the appliances 14, 14a have been placed between pairs of respective guides 40, 40a on the arch model 33. Optionally, the bonding composition used for creating the bonding pads 27 and for temporarily bonding each appliance 14, 14a to the arch model 33 is cured or partially cured before the next appliance 14, 14a is placed on the arch model 33. As yet another option, all of the appliances 14, 14a are placed on the arch model 33 before curing or partially curing any of the bonding composition.

If the appliances 14, 14a are made of metal or another opaque material and if a light-curable adhesive is used as a bonding composition, it is preferable to expose the dental arch model 33 to a curing light for a relatively long amount of time in order to ensure that the bonding composition has sufficiently hardened. A hand-held curing unit may be used, such as Ortholux XT brand curing unit from 3M Unitek Corporation, by directing the light in a labial direction through the crown of each model tooth 34, 34a and toward the base of each appliance 14, 14a for approximately 10 seconds. A LED hand-held curing unit may also be used, such as Ortholux LED brand curing unit from 3M Unitek Corporation by directing the light in the same direction for approximately 5 seconds. As an alternative, a light curing chamber may be used, such as Triad 2000 visible light curing system from Dentsply, by activating the light in the curing chamber for at least 10 minutes. Preferably, the material used to make the arch model 33 transmits actinic radiation to facilitate light in reaching all portions of the bonding composition beneath the base 26 of the appliances 14, 14a.

Preferably, before activating the light source, any adhesive flash that has extruded from the sides of the appliance base 26 is removed using a scaler, probe, swab, brush or high-velocity air stream. Alternatively, however, the adhesive flash may be removed after the adhesive has been partially hardened. Additionally, as another option, the holders 54, 54a may include a support for supporting an air nozzle to supply the high-velocity air stream for removing flash as mentioned above.

The guides 40, 40a are also removed at this time by moving the guides 40, 40a in either a mesial or distal direction away from the adjacent appliance 14, 14a until the legs 52 of the guides 40, 40a fracture and detach from the adjacent ridge 39, 39a. Optionally, the legs 52 fracture at a location directly adjacent the adjoining surfaces of the ridge 39, 39a so that no portion of the legs 52 that remain will protrude from the ridge 39, 39a.

As yet another option, the compressible materials described in published U.S. Patent Application No. 2008/0096150 (Cinader, Jr.) may be used instead of the bonding compositions for creating the bonding pads 27 mentioned above. Advantageously, when using this option the need for removal of adhesive flash is eliminated. In this option, the guides 40, 40a are spaced closer together and the appliances 14, 14a are held in place by friction-fit between the guides 40, 40a while the tray 12 is formed as described in the paragraphs that follow in those instances when the bonding composition is not hardened prior to making the tray 12. Alternatively, when the bonding composition is hardened prior to making the tray 12, the friction fit can be eliminated. To minimize the depth of the impression of the guides 40, 40a in the tray matrix material, the guides 40, 40a are relatively short in length, or are shortened (e.g. by fracture or otherwise) after the appliances 14, 14a are set in place.

Figure 17:
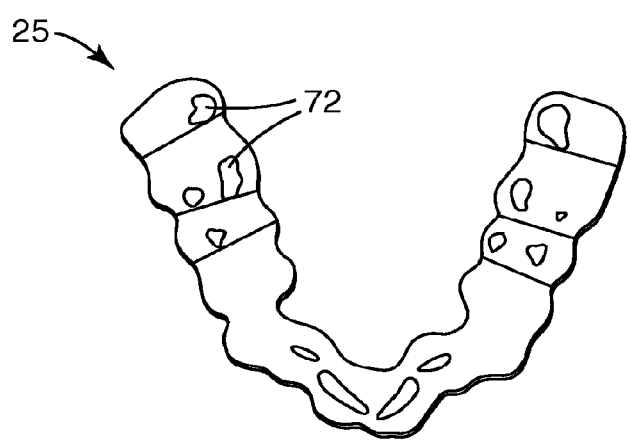
FIG. 17 is a bottom view of an occlusal stop member that is used for making the indirect bonding tray.

FIG. 17 is a bottom view of the occlusal stop member 25. The stop member 25 is preferably made in a rapid prototyping manufacturing process (as described in block 110) simultaneously with the rapid prototyping manufacture of the dental arch model 33 and the tray molding vessel (described below). The occlusal stop member 25 has a flat top surface and a bottom surface with shapes such as recesses 72 that match the shapes of the occlusal tips of the patient's dental arch. In the embodiment shown in FIG. 17, the occlusal stop member 25 has a recess or recesses corresponding to only some of the teeth in the dental arch, although it is also possible to construct an occlusal stop member that has one or more recesses corresponding to each tooth of the dental arch.

Other variations are also possible. For example, the occlusal stop member 25 may extend only along a portion of the dental arch instead of along the entire dental arch as illustrated in FIG. 17. As another option, a plurality of stop members 25 may be provided. For example, a stop member 25 could be provided for each of the two molar regions and a third stop member could be provided for the anterior region of the dental arch. When more than one stop member 25 is provided, the stop members 25 can be spaced apart from each other and optionally connected together.

Figure 18:
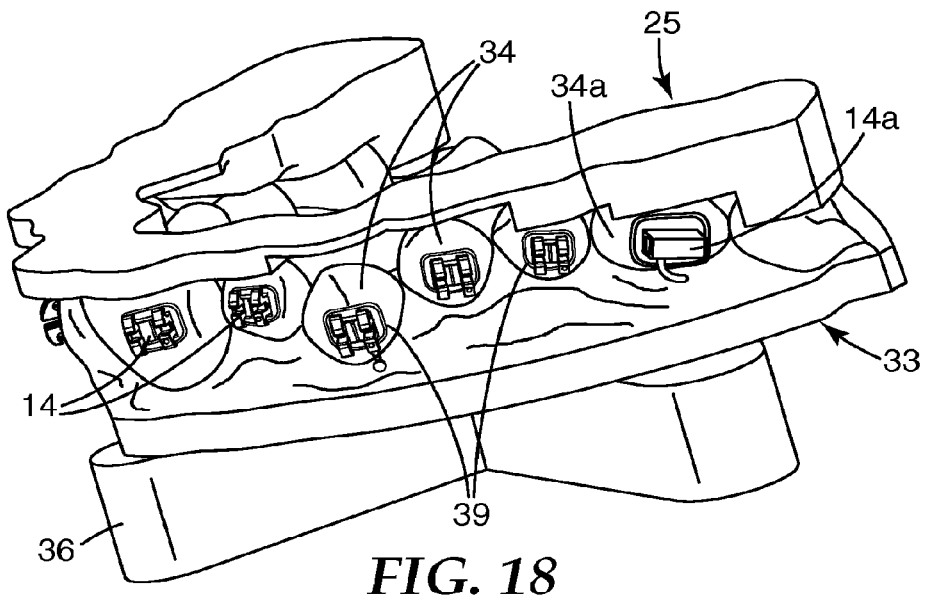
FIG. 18 is a perspective view of the dental arch model and appliances shown in FIG. 16 but looking in a different direction, wherein the guides of the arch model have been removed and the occlusal stop member depicted in FIG. 17 has been placed over occlusal surfaces of the model teeth.

FIG. 18 is an illustration of the arch model 33 after such time as the guides 40, 40a have been detached from the corresponding model teeth 34, 34a and the adhesive flash has been removed. In FIG. 18, the occlusal stop member 25 has also been placed over the occlusal surfaces of the model teeth 34, 34a. Because the recesses 72 match the shape of the corresponding cusp tips of the model teeth 34, 34a, the occlusal stop member 25 can be firmly seated on the arch model 33 in such a manner that little, if any, relative lateral movement is possible between the occlusal stop member 25 and the arch model 33 in directions along an occlusal reference plane.

Figure 19:
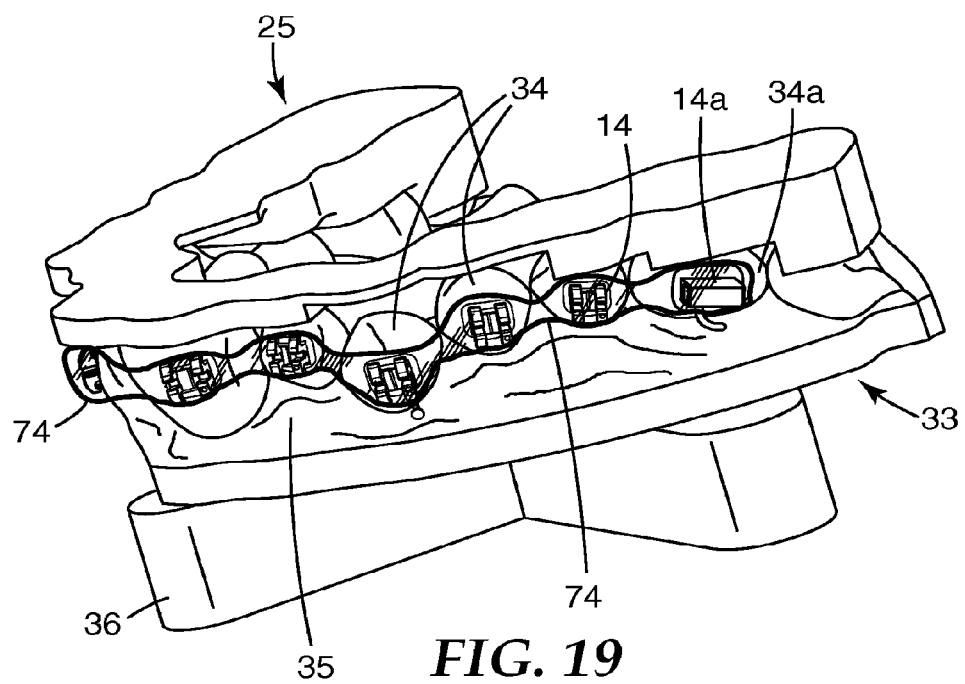
FIG. 19 is a view somewhat similar to FIG. 18 except that a first matrix material has been applied to the orthodontic appliances.

Subsequently, and as described in block 120, a first matrix material is applied to the orthodontic appliances 14, 14a. In the embodiment shown in FIG. 19, the first matrix material 74 has been applied to all of the appliances 14, 14a in the manner of a continuous strip with larger dabs of adhesive over each appliance 14, 14a and smaller necked sections joining the larger dabs, as might occur when a dispenser for the first matrix material 74 is moved from one appliance 14, 14a to the next. However, as another option, the first matrix material 74 may be applied to each appliance 14, 14a as a separate, discreet dab. As still another option, the first matrix material 74 may be applied in the manner of a continuous strip having a relatively uniform width along the entire length of the arch model 33 while covering each of the appliances 14, 14a. Preferably, the first matrix material 74 contacts the occlusal, facial, gingival, mesial and distal sides of the appliances 14, 14a. Optionally, but not necessarily, the first matrix material 74 also contacts at least a portion of the adjacent ridges 39, 39a and possibly also sections of the facial sides of the model teeth 34, 34a that extend along the external sides of the ridges 39, 39a.

Preferably, the first matrix material 74 has a relatively low viscosity before hardening so that intimate contact between the first matrix material 74 and each appliance 14, 14a is assured. In this manner, the first matrix material 74 is able to substantially penetrate in the various recesses, cavities and other structural features of each appliance 14, 14a so that a secure connection between the appliances 14, 14a and the matrix material 74 can be established.

An example of a suitable first matrix material 74 is Emiluma brand silicone material from Shofu Dental Corporation (Kyoto, JAPAN). The matrix material 74 has a viscosity before curing that is preferably less than about 80,000 cp, more preferably less than about 25,000 cp and most preferably less than about 8,000 cp. Once hardened, the matrix material 74 has a tensile stress at 20 percent elongation (according to ASTM D 412) that is in the range of about 31,000 to about 496,000 Pascal, more preferably in the range of about 62,000 to about 248,000 Pascal and most preferably in the range of about 112,000 to about 136,000 Pascal, and has a tensile stress at 50 percent elongation that is in the range of about 91,000 to about 1,460,000 Pascal, more preferably in the range of about 183,000 to about 730,000 Pascal and most preferably in the range of about 329,000 to about 402,000 Pascal. An example of a suitable first matrix material 74 has a tensile stress at 20 percent elongation of about 124,000 Pascal and a tensile stress at 50 elongation of about 365,000 Pascal.

FIG. 20 is a perspective view of a tray molding vessel or casting vessel 76 having an internal cavity 78. Preferably, the tray molding vessel 76 is made by rapid prototyping as described in block 110 simultaneously with rapid prototyping of the dental arch model 33 and the occlusal stop member 25. Optionally, the bottom of the cavity 78 is flat and has a shape that matches the flat top surface of the occlusal stop member 25. In this embodiment, side walls 82 of the vessel 76 that define the cavity 78 extend in a perpendicular direction away from the flat bottom 80, and terminate at the opening of the cavity 78 in a reference plane that lies parallel to the bottom 80. Preferably, the shape of the cavity 78 is minimized as much as practical in order to reduce the overall size of the resulting indirect bonding tray as well as to reduce the amount of material needed to make the tray and the vessel 76.

As an additional option, indicia such as tracking numbers and/or patient data may be formed by rapid prototyping in the tray molding vessel 76, the occlusal stop member 25 and/or the dental arch model 33 during the rapid prototyping process of forming the latter components. Moreover, such indicia can be formed in mirror-image along the inner surfaces of the bottom 80 and/or the side walls 82, so that an imprint presenting a positive image of the indicia is later formed when the indirect bonding tray is made as described below. Alternatively, however, a set of pre-manufactured molding vessels may be used in place of the custom molding vessel described above. For example, a set of vessels could be made to match various standardized archforms, such as the ovoid, standard and square archforms known in the art as described by Drs. McLaughlin, Bennett and Trevisi. In addition, each of the vessels associated with standard archforms could be pre-manufactured in certain sizes, such as small, medium and large.

The tray molding vessel 76 also has a framework that includes alignment structure that, in the illustrated embodiment, comprises a pair of spaced apart posts 84. The posts 84 are matingly received in the alignment holes 38 of the arch model substrate 36 when the arch model 33 is placed into the cavity 78 of the tray molding vessel 76. In this manner, the orientation of the arch model 33 and the resulting indirect bonding tray 12 is fixed relative to the orientation of the cavity 78 in a desired, predetermined spatial relationship. Other constructions for the alignment structure of the tray molding vessel 76 and the arch model substrate 36 are also possible, such as a single post and a single matching hole having non-circular cross-sectional shapes, or other combinations of posts and holes, or a reversal of such components.

A quantity of a second matrix material 86 (not shown in FIGS. 20 and 21; see FIG. 22) is dispensed into in the cavity 78. The arch model 33, together with the appliances 14, 14a and the occlusal stop member 25, is then inverted and placed into the cavity 78 as described in block 122. FIG. 22 is a cross-sectional view of an exemplary model tooth 34, appliance 14, the first matrix material 74 and the occlusal stop member 25 when received in the cavity 78 of the tray molding vessel 76 containing the second matrix material 86.

As depicted in FIG. 22, the second matrix material 86 contacts the labial, occlusal and lingual surfaces of the model teeth 34 except in areas covered by the first matrix material 74 and the occlusal stop member 25. Although not shown in the drawings, the second matrix material 86 optionally contacts at least a portion of the ridges 39, 39a. In addition, the second matrix material 86 extends over and preferably completely surrounds the first matrix material 74 except in underlying areas of the arch model 33. Optionally, the second matrix material 86 extends over the distal ends of the first matrix material 74 adjacent the model molar teeth. The second matrix material 86 also preferably surrounds the occlusal stop member 25 except for those regions of the occlusal stop member 25 that are in contact with the arch model 33. In this embodiment, the stop member 25 is spaced from the first matrix material 74 and separated from the first matrix material 74 by the second matrix material 86.

An example of a suitable second matrix material 86 is Memosil 2 brand vinyl polysiloxane material from Heraeus Kulzer, Inc. The second matrix material 86 has a viscosity before curing that is preferably less than about 1,000,000 cp, more preferably less than about 100,000 cp and most preferably less than about 8,000 cp. Once hardened, the second matrix material 86 has a tensile stress at 20 percent elongation (according to ASTM D 412) that is in the range of about $0.4 \times 10^6$ to about $6.5 \times 10^6$ Pascal, more preferably in the range of about $0.8 \times 10^6$ to about $3.3 \times 10^6$ Pascal and most preferably in the range of about $1.1 \times 10^6$ to about $1.4 \times 10^6$ Pascal, and has a tensile stress at 50 percent elongation that is in the range of about $0.8 \times 10^6$ to about $12.5 \times 10^6$ Pascal, more preferably in the range of about $1.6 \times 10^6$ to about $6.2 \times 10^6$ Pascal and most preferably in the range of about $2.8 \times 10^6$ to about $3.4 \times 10^6$ Pascal. An example of a suitable second matrix material 86 has a tensile stress at 20 percent elongation of about $1.3 \times 10^6$ Pascal and a tensile stress at 50 elongation of about $3.1 \times 10^6$ Pascal.

The second matrix material 86 preferably has a composition that is different than the composition of the first matrix material 74 and after hardening exhibits a tensile stress at 20 percent elongation that is preferably greater than the tensile stress at 20 percent elongation that is exhibited by the first matrix material 74 after hardening. The second matrix material 86 after hardening exhibits a tensile stress at 20 percent elongation that exceeds the tensile stress at 20 percent elongation of the first matrix material 74 after hardening preferably by a ratio in the range of about 2:1 to about 40:1, more preferably by a ratio in the range of about 5:1 to about 20:1 and most preferably by a ratio in the range of about 7:1 to about 12:1. Preferably, the second matrix material 86 chemically bonds to the first matrix material 74 with a relatively high bond strength.

The occlusal stop member 25 is relatively inflexible and has a Shore A hardness that is greater than the Shore A hardness of either of the first matrix material 74 or the second matrix material 86. Preferably, the occlusal stop member 25 has a Shore A hardness that is greater than about 72, more preferably has a Shore A hardness that is greater than about 90, even more preferably has a Shore D hardness that is greater than about 60 and most preferably has a Shore D hardness that is greater than about 75. An example of a suitable hardness is 72 Shore A hardness.

Optionally, the occlusal stop member 25 chemically bonds to the second matrix material 86 as the latter is cured. In addition, or in the alternative, a thin layer of the second matrix material 86 extends over the flat top of the occlusal stop member 25 opposite the side of the stop member 25 facing the arch model 33 in order to physically capture and connect the stop member 25 to the second matrix material 86 once hardened. Moreover, the occlusal stop member 25 may include outwardly-extending barbs or other structure that provides undercut areas for mechanically interlocking the occlusal stop member 25 to the second matrix material 86 once the latter has hardened.

As an alternative, the occlusal stop member 25 is inserted into the cavity 78 of the molding vessel 76 and placed in contact with the vessel bottom 80 before the arch model 33 and the appliances 14, 14a are placed in the vessel 76. In this alternative, a quantity of the second matrix material 86 is dispensed into the cavity 78 either before or after the arch model 33 and the appliances 14, 14a are placed in the cavity 78. As one example, the stop member 25 has a peripheral shape that matches the shape of the side walls 82 so that the stop member 25 is properly aligned with the arch model 33 when the latter is received in the cavity 78. As another example, the stop member 25 has a peripheral shape that is somewhat smaller than the shape of the side walls 82 and instead engages alignment structure of the vessel 76 extending in the cavity 78 for proper, subsequent alignment of the stop member 25 with arch model 33.

The resultant indirect bonding tray 12 is shown in FIGS. 1-4 and comprises the occlusal stop member 25 and the matrix materials 74, 86 once the second matrix material 86 has hardened. The hardened first matrix material 74 forms the inner shell 22 and the hardened second matrix material 86 forms the outer shell 21. The tray 12 together with the appliances 14, 14a is then removed from the molding vessel 76 as indicated by block 124 and the bonding tray 12 and appliances 14, 14a are then removed from the arch model 33. The use of the release agent as mentioned above helps facilitate detaching the tray 12 from the molding vessel 76 and detaching the tray 12 and the appliances 14,14a from the arch model 33. Excess material of the tray 12 is then trimmed as desired as described in block 126 and the tray 12 is inspected before use.

As illustrated for example in FIG. 3, the outer shell 21 formed by the hardened second matrix material 86 presents a lingual, occlusal and facial outer surface that represents the lingual, occlusal and facial sides respectively of the tray 12. In addition, the inner shell 22 (and optionally also adjacent, surrounding portions of the outer shell 21) presents grooves 28 corresponding to the previous location of the ridges 39. Each of the grooves 28 is constructed to receive a quantity of the dental sealant 16, and preferably accumulates a sufficient quantity of the sealant 16 so that a thicker layer of sealant 16 will be transferred to the patient's tooth in areas corresponding to the grooves 28 in comparison to remaining regions of the patient's teeth not covered by appliances 14, 14a.

Preferably, the outermost gingival edge of the tray 12 along the facial side of the tray 12 is located only slightly below the gingival sides of the appliances 14, 14a and spaced in an occlusal direction from the patient's gingival margin a distance of 0.5 mm when the tray 12 is received in place on the patient's dental arch 18 as depicted in FIG. 2. Preferably, the outermost gingival edge of the tray 12 along the lingual side of the tray 12 is spaced about 0.5 mm from the patient's gingival margin when the tray 12 is received in place on the patient's dental arch 18. Such construction facilitates urging the appliances 14, 14a against the patient's teeth 24 during a bonding procedure. The outermost gingival edges of the tray 12 along its facial and lingual sides may be substantially straight or scalloped to follow the contours of the gingival margin.

Figure 23:
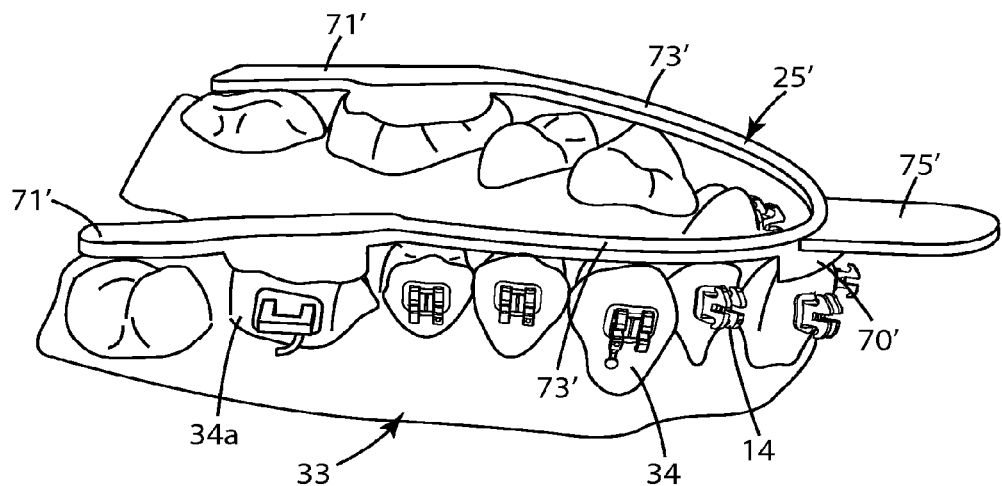
FIG. 23 is a perspective view of an alternative occlusal stop member, wherein the occlusal stop member has been placed over a dental arch model that has received a set of orthodontic appliances.

An occlusal stop member 25' according to another embodiment of the invention is illustrated in FIG. 23. In this embodiment, the occlusal stop member 25' is a single, unitary component but includes four distinct, spaced-apart sections 71' in contact with the occlusal tips of model teeth 34, 34a. Two of the sections 71' are located over posterior regions of the arch model 33 for contact with model molar teeth 34a, while two sections 71' are in contact with two model upper incisor teeth 34. Although not shown in the drawings, each of the sections 71' includes recesses (similar to recesses 72) that matingly receive occlusal tips of the underlying model teeth 34, 34a.

The occlusal stop member 25' also includes an elongated, flexible connecting section 73' that interconnects the anterior sections 71' and the posterior sections 71'. The connecting section 73' has a smaller cross-sectional area and consequently is more flexible than the anterior sections 71' and the posterior sections 71'. In this embodiment, the connecting section 73' does not contact the model teeth 34, 34a and does not include surfaces that match model tooth surfaces.

In addition, the occlusal stop member 25' includes a handle 75' that extends in a facial direction away from the anterior sections 71'. The handle 75' extends past both of the matrix materials once the indirect bonding tray is made, and provides a convenient point of leverage for use by the practitioner when placing the indirect bonding tray onto the patient's dental arch and for removing the indirect bonding tray from the patient's oral cavity after the appliances have been bonded in place. In this embodiment, the tray molding vessel (such as vessel 76) has an opening near the middle of the outer side wall 82 to receive the handle 75' when the occlusal stop member 25' is placed in the vessel. Additionally, the tray molding vessel preferably has a rounded bottom (instead of a flat bottom such as bottom 80) that receives the occlusal stop member 25' in relatively close relation so that the overall size of the resulting bonding tray is reduced.

The flexible connecting section 73' facilitates bending of the resulting indirect bonding tray during use. In particular, the connecting section 73' reduces the amount of finger pressure that might otherwise be necessary for the practitioner to squeeze the posterior regions of the resulting indirect bonding tray in directions toward each other in order to facilitate passage of the indirect bonding tray through the patient's mouth and into the oral cavity. Once the bonding tray is inside the oral cavity, pressure on posterior regions of the tray is released and the connecting section 73' enables the posterior regions of the resilient bonding tray to spring apart and move back to their original configuration so that the tray can then be placed in contact with the patient's teeth.

Preferably, the posterior sections 71' only contact the tooth that is adjacent the distal-most tooth in each side of the dental arch. Preferably, the anterior sections 71' only contact the two mesial-most teeth of the dental arch. Preferably, all of the sections 71' are spaced a distance of at least 0.5 mm from the adjacent appliance 14, but have a thickness that is not greater than necessary so that the resulting thickness of the bonding tray is not unduly affected.

Figure 24:
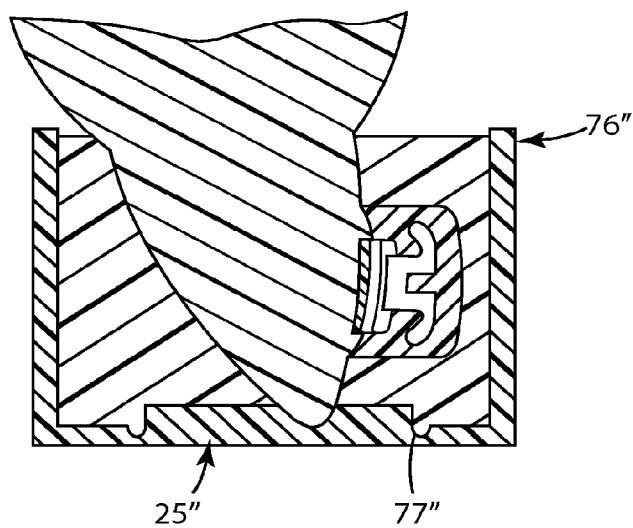
FIG. 24 is a cross-sectional view showing a molding vessel and occlusal stop member of a bonding tray constructed in accordance with another embodiment of the invention.

FIG. 24 is a cross-sectional view of an occlusal stop member 25" and a tray molding vessel 76" that are constructed in accordance with another embodiment of the invention. In this embodiment, the occlusal stop member 25" is initially integral with the tray molding vessel 76" and the occlusal stop member 25" and the tray molding vessel 76" are formed together during rapid prototyping. A line of weakness 77" surrounds the occlusal stop member 25" and defines the boundary between the occlusal stop member 25" and the tray molding vessel 76". After the matrix materials are formed and hardened in a manner similar to the description provided above in connection with FIG. 22 and the tray is removed from the model dental arch, the molding vessel 76" is fractured along the line of weakness 77" and discarded.

As another option, any of the occlusal stop members 25, 25', 25" described above may include a spaced-apart series of arms that each extend in a gingival direction toward a respective appliance 14, 14a. For example, the arms may include an outer end section that is received in the occlusal-gingival or "vertical" channel between tiewings of the appliances 14. These outer end sections help stiffen the resulting tray in rotational directions about its curved central axis and consequently help press the appliances 14 against the patient's tooth surfaces during a bonding procedure.

In addition to the various embodiments described above, other features, constructions and methods are possible. For example, the bonding pad 27 could comprise a partially hardened hardenable composition, such as an adhesive that is 25 percent to 95 percent cured. The term "partially hardened" refers to a partial state of hardening of a hardenable composition, i.e., that the partially hardened hardenable composition is capable of, or can undergo, further hardening. The extent of hardening of a partially or fully hardened hardenable composition relates to the degree of cure of the composition, i.e., to a proportion of reactive chemical groups that have reacted, for example when exposed to actinic radiation to form chemical bonds that increase the molecular weight of the hardenable composition, crosslink the hardenable composition, or both. The degree of cure of a partially hardened hardenable composition can be measurably increased. That is, the proportion of reactive chemical groups that have reacted can be measurably increased when the partially hardened hardenable composition is further exposed to curing conditions such as exposure to actinic radiation. The extent of hardening of the partially hardened hardenable composition can then be determined by relating the degree of cure of the partially hardened hardenable composition to the degree of cure of the composition wherein the proportion of reacted chemical groups does not appreciably or measurably increase when the composition is further exposed to curing conditions.

As an additional option, structure could be added to the bonding tray 12 for controlling moisture control during the bonding procedure, such as described in published U.S. Patent Application No. 2007/0287120 entitled "APPARATUS AND METHODS FOR CONTROLLING MOISTURE DURING ORTHODONTIC INDIRECT BONDING PROCEDURES" and U.S. Pat. No. 7,364,428 entitled "ORTHODONTIC INDIRECT BONDING TRAY WITH MOISTURE CONTROL". The tray 12 may be provided with a flexible cord to fracture the matrix material as described in U.S. Pat. No. 7,020,963 entitled "METHOD AND APPARATUS FOR INDIRECT BONDING OF ORTHODONTIC APPLIANCES". Radio-frequency identification (RFID) tags could be used to track patient-specific materials throughout the manufacturing of the bonding trays 12, as described in U.S. Published Patent Application No. 2006/0134580 entitled "RFID TRACKING OF PATIENT-SPECIFIC ORTHODONTIC MATERIALS". Markers may be used to register virtual and physical dental arches, such as described in U.S. Published Patent Application No. 2007/0031774 entitled "REGISTERING PHYSICAL AND VIRTUAL TOOTH STRUCTURES WITH MARKERS". As another example, instead of the grooves 28 described above, the surface roughness of the model teeth 34 can be increased in areas next to locations corresponding to appliance locations in order to increase the surface roughness of corresponding inner wall portions of the resultant tray 12 and retention of sealant 16 in those areas.

Once the tray 12 is trimmed as mentioned in block 126, the dental sealant 16 is applied to the inner wall portions 23 as described in block 128. Preferably, the dental sealant 16 is applied to the wall portions 23 by the manufacturer before shipment to the practitioner's office. Optionally, the dental sealant 16 is applied as a coating by a spray applicator that directs the sealant 16 toward the wall portions 23 including the grooves 28. A brush may also be used. The coating may have a relatively uniform thickness across the wall portions 23, or alternatively may have an increased thickness in areas defined by the grooves 28.

Interactions may take place between the sealant 16 and the adhesive 29 if they contact each other. For example, in some embodiments, the sealant 16 is miscible with the adhesive 29. Miscibility allows for diffusional mixing to occur at the interface between the sealant 16 and the adhesive 29, leading to improved adhesion and/or an improved "seal" between the two components after hardening. In other embodiments, the sealant 16 is completely immiscible with adhesive 29. Immiscibility can also be advantageous because it can limit the undesirable net diffusion of resin or resin components (also known as "leaching") from sealant 16 into the adhesive 29, or vice-versa. These embodiments may be used in situations where it is critical that the physical and chemical properties of sealant 16 and adhesive 29 do not change over time. In still other embodiments, sealant 16 and adhesive 29 are only slightly miscible with each other, thereby combining the advantages of miscibility and immiscibility. As a further alternative, it is also possible to use the same composition for both the adhesive 29 and the sealant 16. In this case, there is no concentration gradient across the interface between the adhesive 29 and the sealant 16, and therefore no net diffusion would occur. This is applicable in cases where the sealant composition is also well suited for use as an adhesive. For example, this situation may arise when there is close conformity between the bonding pad 27 of the appliances 14, 14a and the patient's tooth surfaces.

Figure 25:
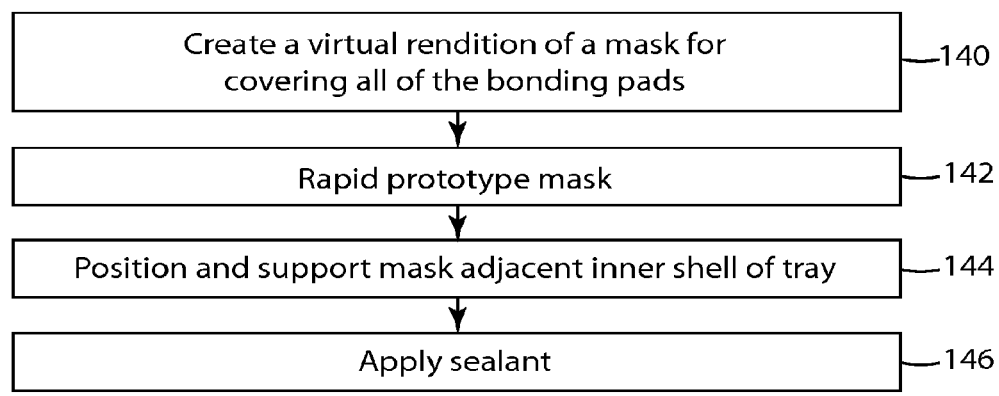
FIG. 25 is a block diagram describing some of the steps that are followed in masking appliances during application of the dental sealant according certain embodiments of the present disclosure.

If the dental sealant 16 is applied as part of a spraying process, the appliances 14, 14a may be masked to avoid contact of the spray with the bonding pads 27. FIG. 25 is a block diagram describing some of the steps that are carried out in one method of creating and masking the appliances, although other methods are also possible. In block 140, the software described above for creating virtual ridges and virtual guides may be used to also create a virtual rendition of a mask in 3D space for covering all of the bonding pads 27. For instance, a single mask could be designed having a plurality of small plates interconnected by a skeletal framework, with each plate have a shape and an orientation relative to other plates for extending over a respective bonding pad 27 of the appliances 14, 14a in the tray 12. In block 142, once the mask is designed by software, the mask may be made using one of the rapid prototyping processes described above, optionally at the same time that the dental arch model 33 is formed. In block 144, the mask is supported in place adjacent the inner shell 22. The dental sealant 16 is sprayed or otherwise applied in block 146. Preferably, the framework of the mask is constructed to provide sufficient space between the framework and the underlying wall portions 23 so as not to unduly hinder the application of a uniform coating of sealant 16 to the wall portions 23.

As yet another option, the sealant 16 may be applied to a model of the patient's dental arch such as the arch model 33 described above. A mask, similar to the mask mentioned above, may be constructed to cover portions of the model that correspond to areas under the bonding pads 27 while the sealant 16 is directed toward the arch model using a spray applicator. Alternatively, the sealant 16 may be applied to the arch model using a brush. The tray 12 is then placed over the arch model in order to transfer the coating of sealant 16 from the arch model to the wall portions 23 of the tray 12. The step of placing the tray 12 could be placed over the model arch to transfer the coating of sealant 16 could be carried out by either the manufacturer of the tray 12 at the manufacturer's facility or by the practitioner in the practitioner's office, optionally using methods similar to the methods described in applying adhesive to the base of appliances in published U.S. patent application no. 2007/0298364 entitled "ORTHODONTIC ADHESIVE DISPENSING ASSEMBLY" (Cinader et al.).

The bonding adhesive 29 is applied to the bonding pads 27 of each appliance 14, 14a, preferably after the sealant 16 has been coated onto the wall portions 23. The bonding adhesive 29 may be applied by hand using, for example, a syringe. Alternatively, an air-powered syringe containing a quantity of the bonding adhesive 29 may be mounted on a robot arm that is programmed to apply the bonding adhesive 29 to each bonding pad 27. The software mentioned above can be used to create instructions for moving the robot arm in 3D space to proper positions for dispensing the bonding adhesive 29 on the bonding pad 27 of each appliance 14, 14a connected to the bonding tray 12

As yet another option, the bonding adhesive 29 and the dental sealant 16 may be the same composition. By using this option, the composition may be applied to the bonding pads 27 and the wall portions 23 simultaneously. For example, the composition may be applied by a brush, or by a spraying process without the need for use of the masks described above. Alternatively, the tray 12 may be placed on a model dental arch containing a quantity of the composition for transfer of the composition to the bonding pads 27 and wall portions 23 simultaneously, either at the manufacturer's facility or in the office of the orthodontic practitioner, optionally using methods similar to the methods described in applying adhesive to the base of appliances in pending U.S. patent application Ser. No. 11/425,461 entitled "Orthodontic Adhesive Dispensing Assembly" (Cinader et al.).

The detailed description set out above is intended to exemplify the invention and a number of other variations are also possible. Consequently, the invention should not be deemed limited to the presently preferred embodiments described above, but instead by a fair scope of the claims that follow along with their equivalents.

The invention claimed is:

1. Orthodontic treatment apparatus comprising:
    an indirect bonding tray including wall portions having a configuration that matches the configuration of at least some regions of a patient's dental arch;
    a set of orthodontic appliances releasably connected to the wall portions;
    a bonding adhesive applied to each appliance for fixing the appliance to a tooth surface of the dental arch; and
    an uncured dental sealant extending across at least some of the wall portions in areas next to the appliances where the bonding adhesive is lacking for transfer to the patient's tooth structure when the indirect bonding tray is placed over the patient's dental arch.

2. Orthodontic treatment apparatus according to claim 1 and including a container, and wherein the indirect bonding tray, the set of appliances and the sealant are enclosed in the container.

3. Orthodontic treatment apparatus according to claim 2 wherein the container comprises a material that substantially hinders the passage of actinic radiation to the dental sealant.

4. Orthodontic treatment apparatus according to claim 3 wherein at least some of the orthodontic appliances include a bonding adhesive for bonding the appliances to the patient's tooth structure.

5. Orthodontic treatment apparatus according to claim 2 wherein the container is sealed to hinder the passage of atmospheric air to areas within the container.

6. Orthodontic treatment apparatus according to claim 1 wherein at least some of the wall portions include a groove that extends at least partially along at least one of the appliances, and wherein at least some of the dental sealant is received in the groove.

7. Orthodontic treatment apparatus according to claim 1 wherein the wall portions include a plurality of grooves, and wherein each groove extends along a path circumscribing a respective one of the appliances.

8. Orthodontic treatment apparatus according to claim 1 wherein the wall portions have a certain surface roughness, and wherein the surface roughness of at least some of the wall portions next to the appliances is greater than the surface roughness of remaining wall portions.

9. Orthodontic treatment apparatus according to claim 1 wherein the wall portions include certain wall portions that match labial, occlusal and lingual regions of the patient's arch and wherein the sealant extends over such certain wall portions.

10. Orthodontic treatment apparatus according to claim 1, wherein the dental sealant extends across wall portions remote from the appliances.

11. A method of providing articles for orthodontic treatment comprising:
    making an indirect bonding tray with wall portions having a configuration that matches the configuration of at least some regions of a patient's dental arch, wherein the act of making the indirect bonding tray includes the act of providing a releasable connection between a set of orthodontic appliances and the wall portions;
    applying a bonding adhesive to each appliance for fixing the appliance to a tooth surface of the dental arch; and
    applying an uncured dental sealant to at least some of the wall portions in areas next to the appliances where the bonding adhesive is lacking.

12. A method of providing articles for orthodontic treatment according to claim 11 and including the act of enclosing the indirect bonding tray, the appliances and the dental sealant in a container.

13. A method of providing articles for orthodontic treatment according to claim 12 and including the act of placing an orthodontic bonding adhesive on the base of at least some of the appliances before the act of enclosing the indirect bonding tray, the appliances and the sealant in a container is carried out.

14. A method of providing articles for orthodontic treatment according to claim 13 and including the act of shipping the container from a location where the indirect bonding tray is made and to a location of an orthodontic practitioner's facility.

15. A method of providing articles for orthodontic treatment according to claim 13 wherein the dental sealant and the orthodontic adhesive are substantially the same composition.

16. A method of providing articles for orthodontic treatment according to claim 11 wherein the act of applying a dental sealant includes the act of spraying the sealant in directions toward the wall portions.

17. A method of providing articles for orthodontic treatment according to claim 16 and including the act of masking at least some of the appliances from the dental sealant while the act of spraying the dental sealant is carried out.

18. A method of providing articles for orthodontic treatment according to claim 11 wherein the act of applying a dental sealant is carried out by:
    providing a model of the patient's dental arch,
    coating at least a portion of the model with the dental sealant, and
    placing the indirect bonding tray over the model in order to transfer at least some of the dental sealant to the wall portions of the indirect bonding tray.

19. A method of providing articles for orthodontic treatment according to claim 11 wherein the wall portions include certain wall portions having a configuration matching at least some of the facial, occlusal and lingual regions of the patient's dental arch, and wherein the act of applying a dental sealant includes the act of applying the dental sealant to such certain wall portions.

20. A method of providing articles for orthodontic treatment according to claim 11 wherein the act of applying a dental sealant to at least some of the wall portions also includes the act of applying the dental sealant to at least some of the appliances.

* * * * *